(12) United States Patent
McNair

(10) Patent No.: US 10,405,810 B1
(45) Date of Patent: Sep. 10, 2019

(54) NONINVASIVE TOOL FOR ASSESSING HYDRATION STATUS

(71) Applicant: CERNER INNOVATION, INC., Kansas City, KS (US)

(72) Inventor: Douglas S. McNair, Leawood, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 388 days.

(21) Appl. No.: 15/162,219

(22) Filed: May 23, 2016

Related U.S. Application Data

(60) Provisional application No. 62/165,888, filed on May 22, 2015.

(51) Int. Cl.
*A61B 5/00* (2006.01)
*A61B 5/053* (2006.01)

(52) U.S. Cl.
CPC .......... *A61B 5/7282* (2013.01); *A61B 5/0015* (2013.01); *A61B 5/053* (2013.01); *A61B 5/4875* (2013.01); *A61B 5/6824* (2013.01); *A61B 5/6831* (2013.01); *A61B 5/746* (2013.01)

(58) Field of Classification Search
CPC ................................................... A61B 5/7282
See application file for complete search history.

(56) References Cited

U.S. PATENT DOCUMENTS

| | | | | |
|---|---|---|---|---|
| 7,561,973 | B1* | 7/2009 | Welch | C12Q 1/6813 435/15 |
| 2005/0039763 | A1* | 2/2005 | Kraemer | A61B 5/0537 600/300 |
| 2007/0203406 | A1* | 8/2007 | Anderson | A61B 5/14551 600/323 |
| 2012/0143019 | A1* | 6/2012 | Russell | A61B 5/0205 600/301 |

FOREIGN PATENT DOCUMENTS

WO    WO-2013184416 A2 * 12/2013  ............. G01R 35/00

OTHER PUBLICATIONS

Price, Kenneth V., et al.; Differential Evolution, A Practical Approach to Global Optimization; Springer-Verlag Berlin Heidelberg, 2005; pp. 1-539. (Hard Cover Book mailed on Feb. 28, 2017 in U.S. Appl. No. 15/291,792).

* cited by examiner

*Primary Examiner* — Daniel L Cerioni
*Assistant Examiner* — Yasmeen S Warsi
(74) *Attorney, Agent, or Firm* — Shook, Hardy & Bacon L.L.P.

(57) ABSTRACT

A tool for predicting that a person is likely to be abnormally hydrated over a future time interval, and in some cases to alert the person or a medical professional to intervene. From a series of physiological measurements, a tissue electrical impedance spectrum curve, which comprises a phase spectrum curve in an embodiment, is determined and changes in the shape of the curve are ascertained. The measurements may be received using one or more sensors worn by the (Continued)

person. In some embodiments, current and historic spectrum curvature are applied to an evolutionary algorithm, such as particle-swarm optimization (PSO) or differential evolution (DE), to determine an inference regarding the persons future hydration status. In one embodiment, a statistical forecast for the next epoch immediately beyond the present one, is determined.

22 Claims, 12 Drawing Sheets

```
##########################################################################

# CERDSM -  Particle Swarm Optimization prediction of dehydration
#              from short EIS phase spectrum curvature time series

##########################################################################
library(pso)

# initialization
# passing NA in e or y[4,4] throws error
# e <- runif(6)  # may not converge
e <- rep(0.01,6)
thresh <- 11.3
pctile <- 0.05 psooptim control, vectorized but still only uses 1 core
ctrl <- list(reltol=2e-01, abstol=5e-01, maxf=1e04, maxit=1e03, maxit.stagnate=1e02,
        vectorize=TRUE, c.p=1.8, c.g=1.8, w=c(0.7,0.9), s=50, p=0.8,
        hybrid=TRUE, hybrid.control=list(maxit=1e03), trace=0, REPORT=1000)
# dsm$par    contains vector of epsilon adjustments
dsm$value contains minimized value of hankel.obj when fnscale=1 alternate control
ctrl <- list(reltol=2e-01, abstol=5e-01, maxf=1e04, maxit=1e03, maxit.stagnate=1e02,
        vectorize=TRUE, c.p=1.2, c.g=1.2, w=c(0.5,0.5), s=30, p=0.5,
        hybrid=TRUE, hybrid.control=list(maxit=1e03), trace=0, REPORT=1000)

# EWMA smoothing
lambda <- 0.7
# inline slightly faster than recursion
ewma6 <- function(s) {
    p1 <- lambda*s[1,2] + (1 - lambda)*s[1,1]
    p2 <- lambda*s[1,3] + (1 - lambda)*p1
    p3 <- lambda*s[1,4] + (1 - lambda)*p2
    p4 <- lambda*s[2,4] + (1 - lambda)*p3
    r <- lambda*s[3,4] + (1 - lambda)*p4
    return(r)
  } hankel objective function
hankel.obj.pso <- function(e) {
    e1 <- e[1]
    e2 <- e[2]
    e3 <- e[3]
    e4 <- e[4]
    e5 <- e[5]
    e6 <- e[6]
               .
               .
               .
```

CONTINUES IN FIG. 4B

*FIG. 4A*

CONTINUES FROM FIG. 4A

.
.
.

```
x11 <- y[1,1]
x12 <- y[1,2]
x13 <- y[1,3]
x14 <- y[1,4]
x21 <- y[2,1]
x22 <- y[2,2]
x23 <- y[2,3]
x24 <- y[2,4]
x31 <- y[3,1]
x32 <- y[3,2]
x33 <- y[3,3]
x34 <- y[3,4]
x41 <- y[4,1]
x42 <- y[4,2]
x43 <- y[4,3]
x44 <- y[4,4]
z <- ewma6(y)
a <- x11 + e1
b <- x12 + e2
c <- x13 + e3
d <- x14 + e4
e <- x24 + e5
f <- x34 + e6
x44 <- ((a*c*e - a*d^2 + b*c*d - e*b^2 + b*c*d - c^3)^-1)*(-d*(b*d*f - b*e^2 + c*d*e - f*c^2 + c*d*e - d^3)
          +e*(a*d*f - a*e^2 + e*c^2 - b*c*f + b*d*e - c*d^2)
          -f*(a*c*f - a*d*e + b*c*e - f*b^2 + b*d^2 - d*c^2))
    y[4,4] <<- x44
    # implement det(x) inline, allowing for mixed double-float and integer numeric storage.mode
       detx <- x11*x22*x33*x44 + x11*x32*x43*x24 + x11*x42*x23*x34
          + x21*x12*x43*x34 + x21*x32*x13*x44 + x21*x42*x33*x14
          + x31*x12*x23*x44 + x31*x22*x43*x14 + x31*x42*x13*x24
          + x41*x12*x33*x24 + x41*x22*x13*x34 + x41*x32*x23*x14
          - x11*x22*x43*x34 - x11*x32*x23*x44 - x11*x42*x33*x24
          - x21*x12*x33*x44 - x21*x32*x43*x14 - x21*x42*x13*x34
          - x31*x12*x43*x24 - x31*x22*x13*x44 - x31*x42*x23*x14
          - x41*x12*x23*x34 - x41*x22*x33*x14 - x41*x32*x13*x24
       abs(detx*(0.1666667*sum(abs(e1),abs(e2),abs(e3),abs(e4),abs(e5),abs(e6)) + abs(x44 - z))^-1)
} hankel matrix examples to solve with y[4,4] non-NULL dummy value, preferably EWMA estimate
may need to add small amount of noise to y to avoid det(x) = 0
# if solver converges, the forecast is value of y[4,4]
# lower and upper parms can be extrema of plausible values
# even if solver does not converge in maxit or maxf, the $par array does contain plausible estimates
for y[3,3]
# iterate N times and take the range as plausible prediction interval for next value y5
```

.
.
.

CONTINUES IN FIG. 4C

*FIG. 4B*

CONTINUES FROM FIG. 4B

```
# function to transform time series 6-vector to matrix for Hankel difference equation model
vec6.trans <- function(v){
 if (length(v) != 6) stop("wrong time series length")
 tmp <- matrix(rep(0,16), ncol=4)
 tmp[1,1:4] <- v[1:4]
 tmp[2,1:4] <- v[2:5]
 tmp[3,1:4] <- v[3:6]
 tmp[4,1:3] <- v[4:6]
 y <<- tmp
} function to calculate 5th percentile of next EIS phase spectrum curvature result from 1000 trials of
Particle Swarm Optimization forecasting of difference equation from 6 previous EIS
psonext.ae <- function(v){
 y5 <- rep(NA, 1000)
 y <- vec6.trans(v)
 y[4,4] <- ewma6(y)
 ul <- mean(y) + 4*sd(y)
 ll <- mean(y) - 4*sd(y)
 for (i in 1:1000) {
  set.seed(as.numeric(Sys.time()))
  dsm <- psoptim(e, hankel.obj.pso, lower=ll, upper=ul, control=ctrl)
  if(dsm$convergence > 0 || y[4,4] < 0)
   {
    y5[i] <- median(dsm$par)
   }else{
    y5[i] <- y[4,4]
   }
 }
 quantile(y5,pctile) < thresh
}
#----------------------------
# true-positive <9.2>
curv <- c(17.3,16.5,12.9,12.3,10.8,9.7)
psonext.ae(curv)

# true-positive <9.9>
curv <- c(13.4,12.3,12.2,13.1,10.4,10.2)
psonext.ae(curv)

# true-positive <71.4>
curv <- c(24.9,25.1,34.2,42.5,51.8,62.7)
psonext.ae(curv)
#----------------------------
# true-negative <18.8>
curv <- c(23.3,31.6,14.3,16.0,16.0,24.9)
psonext.ae(curv)

# true-negative <19.3>
curv <- c(23.1,28.2,24.5,14.1,12.9,22.4)
psonext.ae(curv)

# true-negative <19.1>
curv <- c(17.7,12.9,23.0,22.4,18.9,15.8)
psonext.ae(curv)
#----------------------------
# false-positive <x.x>
#     <none>
#----------------------------
# false-negative <x.x>
#     <none>
```

*FIG. 4C*

```
##########################################################################

# CERDSM - Generate receiver operating characteristic (ROC) curves of dehydration predictions

##########################################################################
library(pROC)
library(DistributionUtils)

# load data  N = 181
ds4 <- read.csv(file="c:/0_cerdsm/IP/conductivity/dehyd.csv")
roc1 <- roc(ds4[,1] ~ ds4[,2], percent=TRUE,
# arguments for auc
#  partial.auc=c(100, 90), partial.auc.correct=TRUE,
#  partial.auc.focus="sens",
# arguments for ci
  ci=TRUE, boot.n=100, ci.alpha=0.9, stratified=FALSE,
# arguments for plot
#  auc.polygon=TRUE, max.auc.polygon=TRUE,
  plot=TRUE, grid=TRUE, print.auc=TRUE, show.thres=TRUE)
sens.ci <- ci.se(roc1, specificities=seq(0, 100, 5))
plot(sens.ci, type="shape", col="lightblue")
plot(sens.ci, type="bars")

# roc(ds4[,1] ~ ds4[,2], ds4, plot=TRUE, col="red")
# AUC 95.1 (91.4 - 98.8)

# column-major
dsm <- matrix(c(47,3,5,126), ncol=2)
fisher.test(dsm)
# chi-sq 139.4  p < 2e-16, OR 353.4
# sensitivity  94% (91-97)
# specificity  96% (93-99)
# PPV          90% (86-95)
# NPV          98% (95-100)
# prevalence   27.6% (21-34)

# population distribution of phase spectrum curvature values
curv <- read.csv(file="c:/0_cerdsm/IP/conductivity/EIS_curvature.csv", header=TRUE,
colClasses=c("numeric"))
hist(curv[,1], breaks=seq(from=0, to=80, by=5))
mean(curv[,1])            # 21
sd(curv[,1])              # 12
sd(curv[,1])/mean(curv[,1])   # 56%
skewness(curv[,1])        # 1.8
kurtosis(curv[,1])        # 3.8
max(curv[,1])             # 78
quantile(curv[,1], 0.95)  # 45
quantile(curv[,1], 0.75)  # 26
quantile(curv[,1], 0.50)  # 17
quantile(curv[,1], 0.25)  # 13
quantile(curv[,1], 0.05)  # 9.3
min(curv[,1])             # 8.5
# approx log-normal
```

*FIG. 4D*

SCHWAN DISPERSION REGIONS

NONINVASIVE TOOL FOR ASSESSING HYDRATION STATUS

CROSS-REFERENCE TO RELATED APPLICATIONS

This application claims the benefit of U.S. Provisional Application No. 62/165,888, entitled "SYSTEM AND NONINVASIVE METHOD FOR ASSESSING HYDRATION STATUS," filed on May 22, 2015, which is incorporated by reference in its entirety.

BACKGROUND

Failure to recognize incipient and emerging dehydration or overhydration leads to adverse outcomes. Potentially life-threatening dehydration occurs frequently. Though less often, serious overhydration also occurs, usually in connection with chronic conditions such as renal disease and dialysis or congestive heart failure. In children, dehydration often leads to unplanned visits to Emergency Departments. In the elderly living in their own homes, significant dehydration often occurs without the person being aware of it; eventually, hypovolemia or electrolyte abnormalities associated with dehydration lead to a state of diminished cardiac output or hypotension, resulting in syncope and falling. In long-term care facilities, dehydration often leads to transfer to a hospital or other acute-care facility and sometimes leads to death.

SUMMARY

A tool for predicting that a person is likely to be abnormally hydrated over a future time interval, and in some cases to alert the person or a medical professional to intervene. The person may be a patient, athlete, or individuals at risk for dehydration, including persons in whom other scores yield excessive false-negative or false-positive results. In particular, an embodiment of the invention acquires physiological data relating to the electrical impedance of human tissue (also referred to as bioimpedance or skin conductance) and ascertains significant changes in the shape of an impedance spectrum curve determined from tissue electrical impedance spectroscopic (EIS) measurement. The impedance spectrum curve may comprise a phase spectrum curve (sometimes referred to as "EIS phase spectrum curvature" value or simply "EIS curve"). Such changes may indicate varying conditions of hydration of the body, with little interference from translational effects caused by other mechanisms. The EIS curve may be determined from measurements using a user-worn sensor and is more likely to be determinable regardless of the anatomical location of the sensor. Some embodiments of the invention comprise utilization of evolutionary time series analytical methods, such as particle-swarm optimization (PSO) and differential evolution (DE) algorithms, in order to provide inferences based on a short time series consisting of a small plurality of observational time points (for example, data from 6 serial measurement epochs).

In one embodiment, the evolutionary analysis estimates the statistical forecast for the next epoch immediately beyond the present one. Some embodiments provide a systems and methods for generating an indicator of a subject's probability of having an abnormal hydration status. One such system may include a data module receiving data relating to a subject's tissue EIS data, a data transformation and statistical computation module generating an output from the data, the output representing the subject's probability of the subject has an abnormal hydration status, and a display module displaying the output. Embodiments may further include a device or apparatus having a processor, one or more sensors, and computer-storage media having a set of computer-executable instructions for determining a subject's probability of an abnormal hydration status.

In this way, embodiments of the invention provide greater accuracy and discriminatory power to classify individual cases correctly when compared to other approaches. Moreover, despite the superior sensitivity to accurately recognize at-risk individuals whose abnormalities are not obvious, embodiments of the invention simultaneously achieve specificity that is superior to the prior art.

BRIEF DESCRIPTION OF THE DRAWINGS

Embodiments of the invention are described in detail below with reference to the attached drawing figures, wherein:

FIGS. 4A-4D illustratively provide example embodiments of a computer program routine used for implementing an embodiment of the invention;

DETAILED DESCRIPTION

Figure 1A:
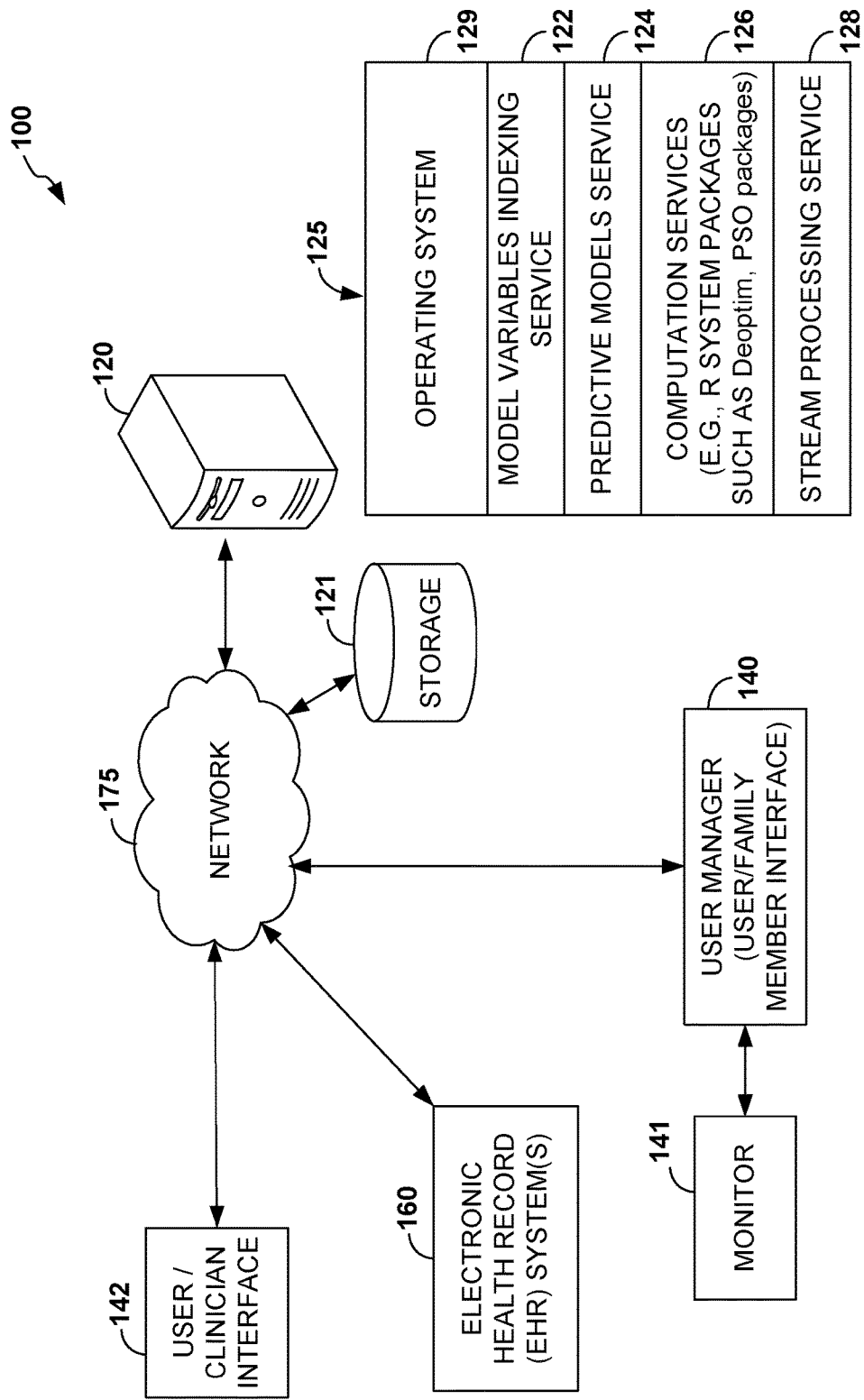
FIGS. 1A and 1B depict aspects of an illustrative operating environment suitable for practicing an embodiment of the invention.

The subject matter of the invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or a set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media can be any available media that can be accessed by a computing device and includes both volatile and nonvolatile media, removable and non-removable media. By way of example, and not limitation, computer-readable media comprises media implemented in any method or technology for storing information, including computer-storage media and communications media. Computer-storage media includes both volatile and nonvolatile, removable and non-removable media implemented in any method or technology for storage of information such as computer-readable instructions, data structures, program modules or other data. Computer-storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by a computing device, such as computing system 900 in FIG. 1B. Computer-storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Accordingly, at a high level, this disclosure describes, among other things, methods and systems for monitoring subjects to quantitatively determine whether or not a significant change in their total body water (TBW) or status of hydration is occurring or has occurred, indicating an abnormal hydration status. Note that for purposes of this disclosure, the term "patient" is sometimes used to describe a subject but that embodiments of the disclosed technology are not limited to a subject being a patient in a medical setting. Among other things, embodiments of the invention may determine significant changes in the shape of an EIS curve indicating varying conditions of hydration of the body, with little interference from translational effects caused by other mechanisms. The EIS curve may be determined from measurement using a subject-worn sensor and is more likely to be determinable regardless of the anatomical location of the sensor. Some embodiments of the invention comprise utilization of evolutionary time series analytical methods, such as particle-swarm optimization (PSO) and differential evolution (DE) algorithms, to provide inferences based on a short time series consisting of a small plurality of observational time points (for example, data from 6 serial measurement epochs). In one embodiment, the evolutionary analysis estimates the statistical forecast for the next epoch immediately beyond the present one. Some embodiments ascertain a state of abnormal hydration, such as dehydration or overhydration, in a timely, usable fashion, preferably before a 5% exceedance of normal values has occurred, so that preventative interventions may be undertaken and adverse events prevented. Moreover, some embodiments of the invention comprise predictive or anticipative, proactive aspects for managing hydration (fluid retention) that can be implemented in the home or other ambulatory settings, rather than requiring direct observation, time-consuming testing, special instrumentations in a medical facility.

As described above, potentially life-threatening dehydration and serious overhydration may occur often. For some populations of subjects, such as children and older adults, dehydration is a difficult diagnosis because the physical signs of dehydration are often confusing. Yet, the consequences of a diagnosis of dehydration are critical because dehydration implies increased morbidity and mortality and aggressive rehydration can improve the outcome. The diagnosis of dehydration is a sentinel event for nursing homes and often is made at transfer to a hospital. Symptoms of dehydration, such as decreased subclavicular and thigh skin turgor, dry oral mucosa, or recent changes of consciousness, are not observed in all individuals. Among subjects with a medical diagnosis of dehydration, only 17% have a serum osmolarity greater than 295 mOsm, and only 11% have a serum sodium level greater than 145 mmol/L. Additionally, a BUN-to-creatinine ratio greater than 20 is present in only approximately 65% of the subject. Medical professionals appear to be using the term "dehydration" synonymously with intravascular volume depletion. Even so, at least a third of the diagnoses of intravascular volume depletion in older adults are incorrect based on laboratory data. Physicians who diagnose dehydration during hospital admissions may be relying more on physical signs instead of laboratory data, but, in doing so, they are likely missing more than 30% of individuals who have medically significant dehydration.

Fluid overload, also referred to herein as overhydration, presents similar difficulties of diagnosis. Such diagnosis difficulties are particularly present in individuals with chronic kidney disease or congestive heart failure or other heart disease. There is a narrow margin of optimal hydration for heart failure patients. Overhydration can cause decompensation of heart failure, leading to hospital admittance, just as dehydration or reduction of intravascular volume can cause distant organ damage via inadequate perfusion.

Major problems in delivery of safe and effective care services in hospitals involve deficiencies in the quality and continuity of patient care, including the monitoring of each individual's condition over time. Despite recent advances in electronic medical records (EMR) systems, the present state of the art in medical care still does not in general utilize the accruing medical record information for active, prognostic use-cases to predict the future status or events or outcomes that are likely to materialize for the individual. Instead, in many scenarios, the EMR acts mainly as a passive repository for documenting and storing the information that is generated by each provider and each department, which characterizes the current or previous status or outcomes that have already materialized.

During ongoing care management in situations requiring attentiveness to hydration status, such as athletic activity or medical conditions such as renal disease, heart failure, or dementia, each person may see many different athletic trainers or medical professionals over a period of time. This fragmentation of responsibility for the care process often divides responsibility among dozens of provider personnel, most of whom do not have deep or longstanding familiarity with the individual. This fragmentation of the care process challenges the ability of each provider to quickly and accurately grasp the meaning of the constellation of accumulating medical and laboratory facts about the individual to understand trends that may be developing in the individual's health status and to evaluate the urgency of attention that is necessary to effectively address existing or newly developing issues and successfully prevent potential adverse events and complications.

The consequence of relatively infrequent assessment of hydration status, when combined with the all-too-common fragmentation of the care process, is an unexpected deterioration of an individual's hydration state such that a medical crisis ensues. In many such instances, the impending deterioration could have been predicted—provided that more frequent hydration monitoring data were acquired in advance; provided that that data were integrated into a suitably accurate personalized predictive model; and provided that the output of the model were effectively communicated to the family members or providers who have the responsibility to intervene and prevent or manage the predicted risk of deterioration.

Subtle patterns in tissue electrical impedance spectroscopic (EIS) measurements may signal departures from the normal range for hydration, which in turn can lead to adverse events such as syncope and falling. Early detection of such EIS patterns may lead to prevention or at least more timely treatment. But early detection cannot occur unless EIS or other variables are measured with sufficiently frequently. Frequent measurement is a strategy that has often been neglected but is now more feasible with wearable, internet-connected devices that are provisioned with multiple onboard sensors. The time series comprised of serial EIS measurements may evolve relatively rapidly on a time-scale of 24 hours depending on the nature and severity of the emerging hydration derangements. Some embodiments of invention apply Hankel matrix equations representing short time series of such values as an algebraic evolution and, thereby, produce accurate forecasts of near-term future values. A suitable solver for such equations will involve an objective function including minimizing the determinant of the Hankel matrix.

Probability distributions whose moments (expected value, variance, etc.) are time-invariant are known to be stationary distributions. If the distribution of objective function fluctuations is stationary and its expectation value is finite, then the optimal vector and the objective function can be reliably and accurately estimated. But the probability distributions of EIS signals is, in general, non-stationary and is particularly so in the context of acute medical care where a person is experiencing some organ system state that is sufficiently abnormal to warrant presenting to the medical system for care or seeking guidance from caregivers who are able to manage the individual's hydration.

When an objective function's minimum is non-stationary, its moving average location drifts and the optimization goal is one of tracking the optimal vector on short sequences of observations, short time-scales, or both. In the case of acute-care monitoring where the status of the individual often changes relatively quickly, the optimum may drift rapidly. Further, the systems that give rise to the measured data tend to embody a chaotic, stochastic process for which least-mean-square or recursive least-square deterministic optimizer that requires estimating a derivative with respect to time does not produce forecasts of adequate accuracy.

Embodiments of the invention may comprise systems and methods that can accommodate rapid-drift non-differentiable processes. In particular, some embodiments initialize algebraic evolution solvers staggered in time. These solvers may operate in parallel, and each successively converges and returns its result to another solver that combines a plurality of the serialized results into a combined ensemble forecast for the value that will be measured at the next observation. The invention does not require that the serial measurements be made at precise, periodic intervals but, instead, tolerates significant clock or phase jitter in the measured time series.

Moreover, some embodiments overcome certain drawbacks associated with the prior art by providing a means for longitudinally calculating and tracking the subject's risk of acute deterioration while in a hospital. Systems and methods for providing a predicted probability of acute deterioration for an ambulatory person, such as an athlete or a resident of a long-term care facility, or a hospitalized patient, are disclosed herein.

According to aspects described herein, there is provided systems and methods for generating an indicator of a subject's probability of an abnormal hydration status. The system may include a data module receiving data relating to a subject's tissue EIS data, a data transformation and statistical computation module generating an output from the data, the output representing the subject's likelihood of deteriorating acutely, and a display module displaying the output. Embodiments may further include a device or apparatus having a processor, one or more sensors, and computer-storage media having a set of computer-executable instructions for determining the subject's probability of an abnormal hydration status.

Particle swarm optimization (PSO) is an algorithm that performs population-based stochastic search and optimization. It originated from computer simulation of individual 'particles', such as members of a flock of migratory birds flying or a school of fish swimming Swarms consisting of many individuals establish an overall direction of movement, collectively and socially, in a self-organizing manner that responds to optimum directions initially undertaken by one or a few individual members. Each particle keeps track of its own position in the search space and of its own best solution so far achieved. The PSO process also keeps track of the globally best solution achieved by the swarm.

During the exploration across the search space with discrete time iterations, the velocity of each PSO agent is computed as a function of the best position of the swarm, the best personal position of each particle, and its previous velocity. These components contribute randomly to the position of each particle in the next iteration or generation of the swarm. Together, the generations exhibit a tendency toward survival of the fittest and global best in terms of minimizing the objective function. The probability of success is increased due to the large number of particles in the swarm because success requires merely that one member of the swarm succeed. As such, PSO is able to efficiently discover correct global optima even when presented with optimization search spaces that have many local minima and nonlinearities or discontinuities.

Differential evolution (DE) is an evolutionary algorithm that has similarities to so-called genetic algorithms (GA). But DE has certain differences insofar as it is applicable to real-valued vectors rather than bit-encoded strings. Accordingly, the DE algorithm's mutation and cross-over operations are different from those in GA. Notably, the mutation operator is different in its way of becoming trapped in local minima of the function being optimized. Like PSO, DE has population members or agents that effectively sample the search space of possible function values. For each successive generation of agents, mutation and cross-over operators are applied to each agent's vector, a numerical objective function fitness is calculated, and the best of that generation's members are propagated to the next generation. This process is repeated until the fitness converges to an asymptotic value. If any agent achieves the objective fitness score or the maximum number of generations set as a limit, then the process is terminated.

In the context of the present invention, DE and PSO and similar evolutionary algorithms that are known to those practiced in the art may be used to predict abnormal hydration status. Each evolutionary algorithm appears to possess strengths and limitations as they concern particular applications in hemostasis variables forecasting. Regardless which of these algorithms is employed by an embodiment of the invention to solve the optimization, the various embodiments of the invention may apply algebraic evolution formalism utilizing Hankel matrices and objective functions of the type disclosed herein. PSO and DE have been utilized to numerically solve other equations relating to phenomena in nonlinear wave motion, soliton physics, Kortweg-de Vries equations, Kadomtsev-Petviashvili equations, and the nonlinear Schrödinger equation.

In acute-care settings, hydration status may be assessed qualitatively by observing skin turgor, sunkenness of the eyes, and other physical exam measurements. Laboratory tests, such as serum or urine osmolality or urine specific gravity, are also used. Similarly, in dialysis and other chronic care situations, whole-body electrical impedance spectroscopy or bioimpedance may be used to assess hydration status. However, those prior art methods have numerous limitations and/or inaccuracies such as described herein. In particular, a significant limitation of the prior art is that it suffers from limited statistical sensitivity and specificity with substantial false-negative and false-positive rates.

A further limitation is a requirement for positioning sensors on the body in such a configuration (such as leg-and-arm or leg-and-thorax) so as to make continuous or frequent, repeated measurements impracticable in an ambulatory subject. Yet another limitation of the prior art is that the variables that are included in the predictions are often temporally 'lagging indicators' (such as serum total protein or osmolality or urine specific gravity), such that the determinations are only capable of ascertaining dehydration or overhydration after these have become medically significant. Still another limitation of the prior art is that the measurement systems and methods involve equipment that is only suited to use by experienced personnel in a physician office, a hospital or other health/medical service locations. In other words, such equipment is not practical for use in the subject's home. Measurement technology in this equipment is not amenable to embodiment in small, wearable monitoring devices such as fitness bands or sports wristwatches. Further, some of the prior art is comprised of laboratory tests (e.g., osmolality) that are not routinely available even in ambulatory clinics, physician offices, or long-term care locations and are of a complexity such that it is improbable that any embodiment will ever become available for use in the home or other residential settings. Still another limitation of the prior art is that of excessive variability in determinations based on gender, age, varied skin type in various anatomical locations, stratum corneum thickness in different locations, skin pigmentation, sweat gland areal density in the skin in the regions sampled by sensors, body core temperature and peripheral skin temperature in the regions sampled, or degree of perspiration in said regions.

Another limitation of prior art involving galvanometry or impedance measurements is that of excessive variability arising due to inconsistent disposition of sensor surfaces in successive measurements where the user stands on sensor surfaces with the feet or grasps sensor surfaces with the hands but does so in significantly different manner from instance to instance, in different orientations, and/or with different pressure applied to the sensor by the body part(s).

Electrical impedance may expressed in terms of its magnitude, phase, or as a complex impedance that reflects both magnitude and phase. Each of these may be measured on a spectrum and may be affected by the variations discussion. For example, variations in skin structure cause the electrical impedance magnitude spectrum on a Bode plot (see e.g., FIG. 5B) to be shifted right or left or be translated upward or downward in the log-resistivity-log-frequency plane. Such variations constitute 'noise' that has limited the accuracy of prior art analytical methods. Likewise, variations, such as in sensor placement skin and subjacent tissue structure, may cause the phase spectrum to be translated in the phase-angle-log-frequency plane, interfering with prior art attempts to interpret the spectrum. However, as described herein, embodiments of the disclosed technology utilize methods for ascertaining significant changes in the shape of the EIS curve as are found to occur, regardless of anatomical location, with little interference from translational effects caused by other mechanisms. The changes in the shape of the EIS curve may be that of the phase spectrum, the magnitude spectrum, or of the complex EIS curve. Such changes may be indicative of varying conditions of hydration of the body.

Another limitation of some of the prior art is that it relies on "wet" electrode sensors, requiring conductive electrode gel or paste to be applied to the skin where measurements are to be made. Use of wet electrode sensors entails mess and inconvenience in applying and removing the gel or paste, and it precludes continuous or prolonged intermittent measurements in a "wearable" arrangement due to skin irritation by the gel or paste.

As a consequence of the foregoing, the prior art has the limitation that it is applied only infrequently, as opposed to daily or multiple times within each day, and, as a result, numerous occurrences of an abnormal hydration state do materialize. Accordingly, these prior approaches are chiefly valuable only for diagnosis but not for prevention.

As described above, embodiments of the invention may predict an abnormal hydration status in subjects, including patients, athletes, other individuals at risk, or persons in whom other scores yield excessive false-negative or false-positive results. Moreover, despite a superior sensitivity to accurately recognize at-risk individuals whose abnormalities are not obvious, embodiments of the invention simultaneously achieve specificity superior to the prior art. In particular, for one embodiment constructively reduced to practice, the ROC AUC is greater than 90% in the populations examined, as illustratively provided in FIG. 3. In part, this greater accuracy and discriminatory power to classify individual cases correctly is due to the utilization of evolutionary time series analytical methods, such as particle-swarm optimization (PSO) and differential evolution (DE) algorithms, which enable inferences based on a short time series consisting of a small plurality of observational time points (for example, data from as few as 6 serial measurement epochs). In some embodiments, an evolutionary analysis estimates the statistical forecast for the next epoch immediately beyond the present one.

There are some changes in hydration status that are acute, with sudden onset and no apparent antecedent abnormality or multivariate cluster of abnormalities that predict the imminent event. Fortunately from the screening and diagnostic perspective, a majority of subjects who deteriorate have a prodrome of abnormalities for many hours in advance of the onset of deterioration. This affords a "window of opportunity" sufficient for undertaking effective preventive and corrective actions, such as intensified monitoring, so as to intervene more quickly and effectively than would otherwise tend to occur.

In many instances, the prodrome involves a change in statistical relationships (e.g., autocorrelation of one variable with itself; cross-correlations between pairs of variables) that bear on the natural physiologic coupling between the organ systems and processes that give rise to the measured variables (for example, the relation of osmolality to central venous pressure, embodied in composite functions of these variables, such as osm*CVP in the context of acute care). The statistical distributions of the values taken on by the terms in such derived, composite variables are both skewed and asymmetric, under both normal conditions and various pathophysiologic conditions that give rise to actionable events that relate to medical outcomes. However, the practical reality is that statistical tests of the goodness-of-fit of distributions to data require a considerable number of observations in order to produce a reliable conclusion or p-value. But in some embodiments of the invention, the model development dataset and model validation dataset were able to generate stable, reliable p-values for PSO or DE forecasts based on as few as 6 measurements, primarily of the derived variable, impedance phase spectrum curvature. Such reliable values may also be achieved for PSO or DE forecasts based on 4 to 8 measurements.

As described previously, the failure to recognize incipient and emerging dehydration or overhydration, especially for individuals in general hospital wards, leads to adverse outcomes. Earlier intervention, prevention of deterioration, and improvement in subject outcome may require a series of steps including vital sign documentation and interpretation; subsequent meaningful communication and timely and appropriate medical management. Embodiments of the invention avoid most of the limitations of the prior art and achieve superior predictive accuracy and statistical discrimination compared to other scores. For some embodiments, this superior performance is due in part to (a) analyzing physiologic time series as arising from an 'algebraic evolution' and (b) processing the resulting array of information so as to generate a predicted value for the time series at one or more future time points.

Figure 5A:
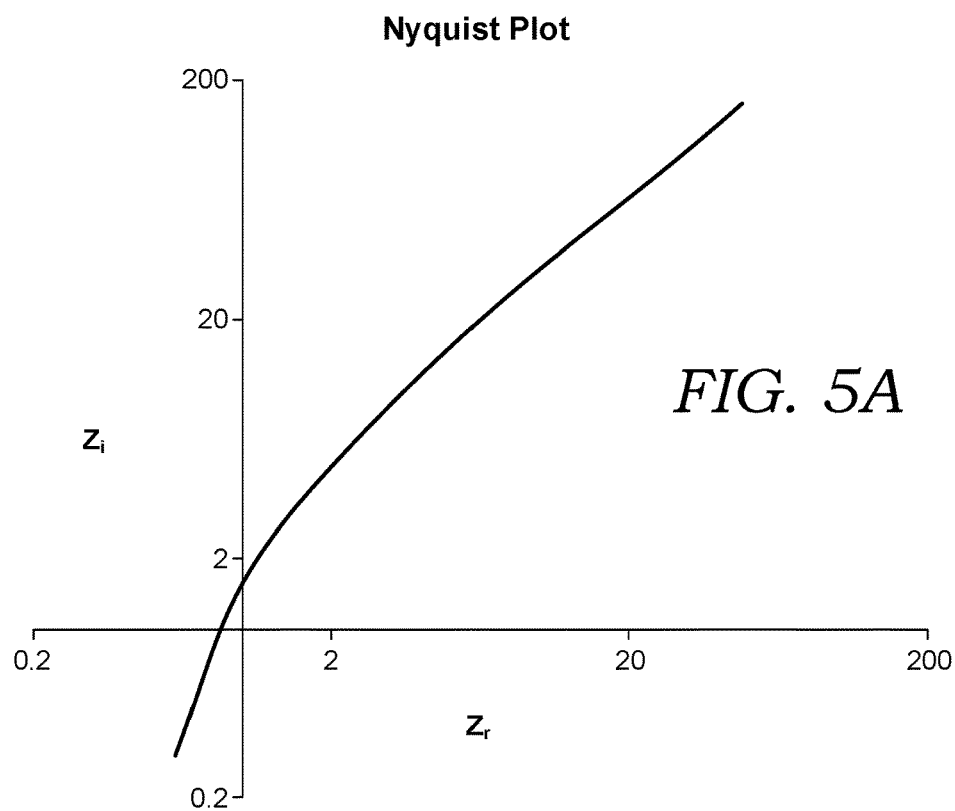
FIGS. 5A and 5B depicts a Nyquist plot and Bode plot, respectively, of skin impedance.
Figure 6:
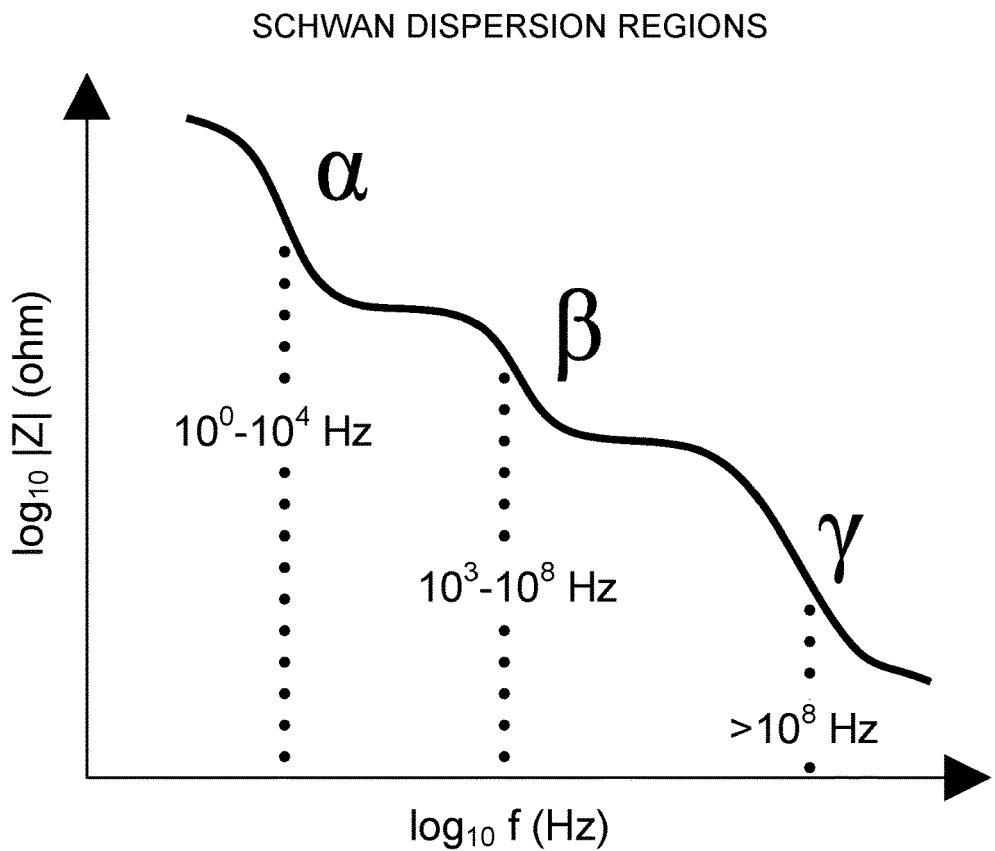
FIG. 6 depicts the Schwan dispersion regions for bioimpedance spectra.

Bioimpedance spectra, plotted in a Nyquist plot (e.g., FIG. 5A) of real and imaginary components of the impedance, reveals a pattern of convex-upward regions, and each convexity corresponds to a particular dispersion mechanism and the molecules and structures that participate in it. With reference to FIG. 6, in the 1950s, H.P. Schwan termed the major convexities in this pattern alpha-, beta-, and gamma-dispersions. The alpha region (1 Hz to 10 KHz) involves mainly polarization of ionic clouds of solutes in the interstitial fluid surrounding cells. The beta region (10 KHz to 100 MHz) is associated with edema, polarization of cell membranes, and structure changes in cell membranes. The gamma region (100 MHz to 1 GHz) is determined by rotational movements of water and other small polar molecules, as shown in FIG. 6. The stratum corneum heavily dominates the electrical impedance at low frequencies around 1 kHz, which suggests that the potential drop over the viable skin is negligible and that the complete potential drop occurs over the stratum corneum.

Accordingly, some embodiments of the invention provide systems and methods for continually tracking the medical and physiologic status of a human subject, particularly in the non-medical care locations. At least some embodiments allow the subject, family-member caregivers, physicians, nurses and medical researchers to provide safer and more effective care for each such subject by utilizing bioimpedance spectroscopy data acquired via sensor-equipped, internet-connected wearable devices, such as sports watches. In addition or alternatively, at least some embodiments assist hospitals in preventing and reducing the frequency of crises in dehydration or overhydration by using the systems' capability to recognize trends in a person's hydration status before the person deteriorates or reaches a crisis.

Recognizing a high risk of deterioration far enough in advance of the onset of deterioration (i.e., the abnormal hydration status) can guide rational allocation of resources, including intensified monitoring or treatments that may achieve reduction of risks of dehydration or overhydration events, decreased length-of-stay in acute care institutions, financial savings, or other benefits. Some embodiments of the present invention generate near-term forecasts that may be periodically plotted and displayed to show each person's risk trend during his/her fluids management. Some embodiments of such systems may include an interface module for receiving incoming medical data from a person, a transformation module for transforming the medical datum into forecasted value, and a combination module for combining successive forecasts of electrical impedance phase spectrum curvature into a single value.

As previously mentioned, prior approaches using electrical impedance spectroscopy have been limited in accuracy and clinical utility by the effects of nevi and other skin lesions on the impedance sensors; by variations in the thickness of stratum corneum within person and between persons; by eczema, psoriasis, hyperhidrosis, other skin conditions; by the person's use of anionic and cationic soaps and detergents, moisturizers, lotions, abrasives, peels, and other skin-care products.

It has further been shown that the skin impedance varies in characteristic patterns among different anatomical locations, by season and humidity level, and by age and gender. These variations cause the impedance magnitude spectrum on a Bode plot to be shifted right or left or be translated upward or downward in the log-resistivity-log-frequency plane. Such variations constitute 'noise' that has limited the accuracy of prior art analytical methods. Likewise, variations such as the foregoing may cause the phase spectrum to be translated in the phase-angle-log-frequency plane, interfering with prior art attempts to interpret the spectrum. However, as previously described, some embodiment of the invention involve determining statistically significant changes in the shape of the spectrum curve (i.e., the curvature), which occur, regardless of anatomical location, with varying conditions of hydration of the body with little interference from translational effects caused by other mechanisms.

Referring now to the drawings in general, and initially to FIG. 1A in particular, an aspect of an operating environment 100 is provided suitable for practicing an embodiment of the invention. Certain items are shown in block-diagram form more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus, for readability, we show and reference items in the singular while fully contemplating, where applicable, the plural.

As shown in FIG. 1, example operating environment 100 provides an aspect of a computerized system for compiling and/or running aspects of the invention, which, at a high level, may include a data interface module for receiving incoming medical data from a subject, such as a subject's tissue EIS data, a transformation module for transforming the medical datum into forecasted value representing the subject's likelihood of experiencing an abnormal hydration status, a combination module for combining successive forecasts of EIS curvature (including phase spectrum) into a single value, and, in some embodiments a display module displaying the output.

Environment 100 includes one or more electronic medical record (EMR) systems, such as a hospital's EMR system 160, communicatively coupled to network 175, which is communicatively coupled to computer system 120. As used herein, EMR systems includes electronic health records systems. In some embodiments, components of environment 100 that are shown as distinct components may be embodied as part of or within other components of environment 100. For example, EMR system 160 may comprise one or a plurality of EMR systems such as a personal medical record system, hospital EMR systems, medical information exchange EMR systems, ambulatory clinic EMR systems, psychiatry/neurology EMR systems, and may be implemented in computer system 120. Similarly, EMR system 160 may perform functions for two or more of the EMR systems (not shown).

Network 175 may comprise the Internet, and/or one or more public networks, private networks, other communications networks such as a cellular network, or similar network(s) for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments items shown communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of EMR system 160 include one or more data stores of medical records, which may be stored on storage 121, and may further include one or more computers or servers that facilitate the storing and retrieval of the medical records. In an embodiment, the medical records comprise a personal medical or health record for a subject or patient. In some embodiments, EMR system 160 may be implemented as a cloud-based platform or may be distributed across multiple physical locations. EMR system 160 may further include record systems, which store real-time or near real-time subject (or user) information, such as subject monitor 141, which may comprise one or more wearable, bedside, or in-home patient monitor(s), for example.

Example operating environment 100 further includes an interface 142 communicatively coupled through network 175 to an EMR system 160. Although environment 100 depicts an indirect communicative coupling between interface 142 and EMR system 160 through network 175, it is contemplated that an embodiment of interface 142 is communicatively coupled to EMR system 160 directly. An embodiment of interface 142 takes the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet.

The user interface may be displayed on a sensor device acquiring data and viewable by the subject. In addition or alternatively, the user interface may be on a device used by a third-party, such as the subject's medical provider. Medical provider, as used herein, includes medical professionals and healthcare providers. A provider application facilitates accessing and receiving information from a user or medical provider about a specific subject or set of subjects. Embodiments of interface 142 also facilitates accessing and receiving information from a user or medical provider about a specific subject or population of subjects, including subject's history; medical care resource data; variables measurements, time series, and predictions (including plotting or displaying the determined outcome and/or issuing an alert) described herein; or other health-related information, and facilitates the display of results, recommendations, or orders, for example. In an embodiment, interface 142 also facilitates receiving orders for the subject from the medical professional or user, based on the results of monitoring and predictions. In some embodiments, interface 142 may also be used to display a subject's hydration status, forecast, or related information. Interface 142 may also be used for providing diagnostic services or evaluation of the performance of various embodiments.

Example operating environment 100 further includes computer system 120, which may take the form of a server that is communicatively coupled through network 175 to EMR system(s) 160 storage 121, and user manager 140.

Embodiments of user manager 140 may take the form of a user interface and application, which may be embodied as a software application operating on one or more mobile computing devices, tablets, smart-phones, front-end terminals in communication with back-end computing systems, laptops or other computing devices. In some embodiments, manager 140 includes a Web-based application or set of applications that is usable to manage user services provided by embodiments of the invention. For example, in some embodiments, manager 140 facilitates processing, interpreting, accessing, storing, retrieving, and communicating information acquired from monitor 141. In some embodiments, manager 140 is used to display user (or subject) bioimpedance information. Similarly, a user may access and view records of hydration (fluid retention) or analyses using manager 140. Moreover, in some embodiments of manager 140, an interface component may be used to facilitate access by a user to functions or information on monitor 141, such as operational settings or parameters, user identification, user data stored on monitor 141, and diagnostic services or firmware updates for monitor 141, for example.

As shown in example environment 100, manager 140 is communicatively coupled to monitor 141 and to network 175. Embodiments of monitor 141 comprise one or more sensor components operable to acquiring biometric information about a user, such as physiological data associated with the subject's hydration status (fluid retention), and that may be acquired continuously, periodically, as one or more time series, or on an as-needed basis. In some embodiments, monitor 141 comprises a sensor component operable for sensing a skin conductance or electrical impedance. In some embodiments, one or more sensor components of monitor 141 may comprise a user-wearable sensor component or sensor component integrated into the user's or subject's living environment. Examples of sensor components of monitor 141 include wherein the sensor is positioned on or near the user's head, attached to the subject's clothing, worn around the subject's head, neck, leg, arm, wrist, ankle, etc., skin-patch sensor, ingestible or sub-dermal sensor, or wherein sensor component(s) are integrated into the subject's living environment (including the bed, pillow, or bathroom), and sensors operable with or through a smart phone carried by the subject, for example.

Embodiments of monitor 141 may store subject-derived data locally or communicate data over network 175 to be stored remotely. In some embodiments, manager 140 is wirelessly communicatively coupled to monitor 141. Manager 140 may also be embodied as a software application or app operating on a user's mobile device. In some embodiments, manager 140 and monitor 141 are functional components of the same device, such as a device comprising a sensor and a user interface. In some embodiments, manager 140 is embodied as a base station, which may also include functionality for charging monitor 141 or downloading information from monitor 141.

Figure 7A:
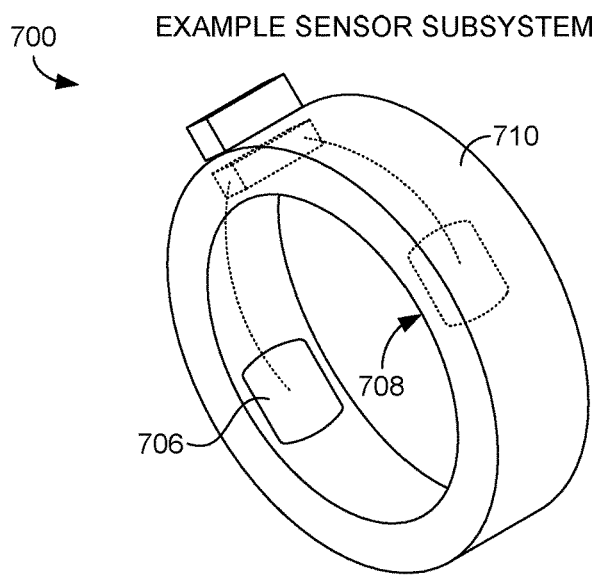
FIGS. 7A-7B depict aspects of one example of a sensor and data acquisition component for use in an embodiment of the invention.
Figure 7B:
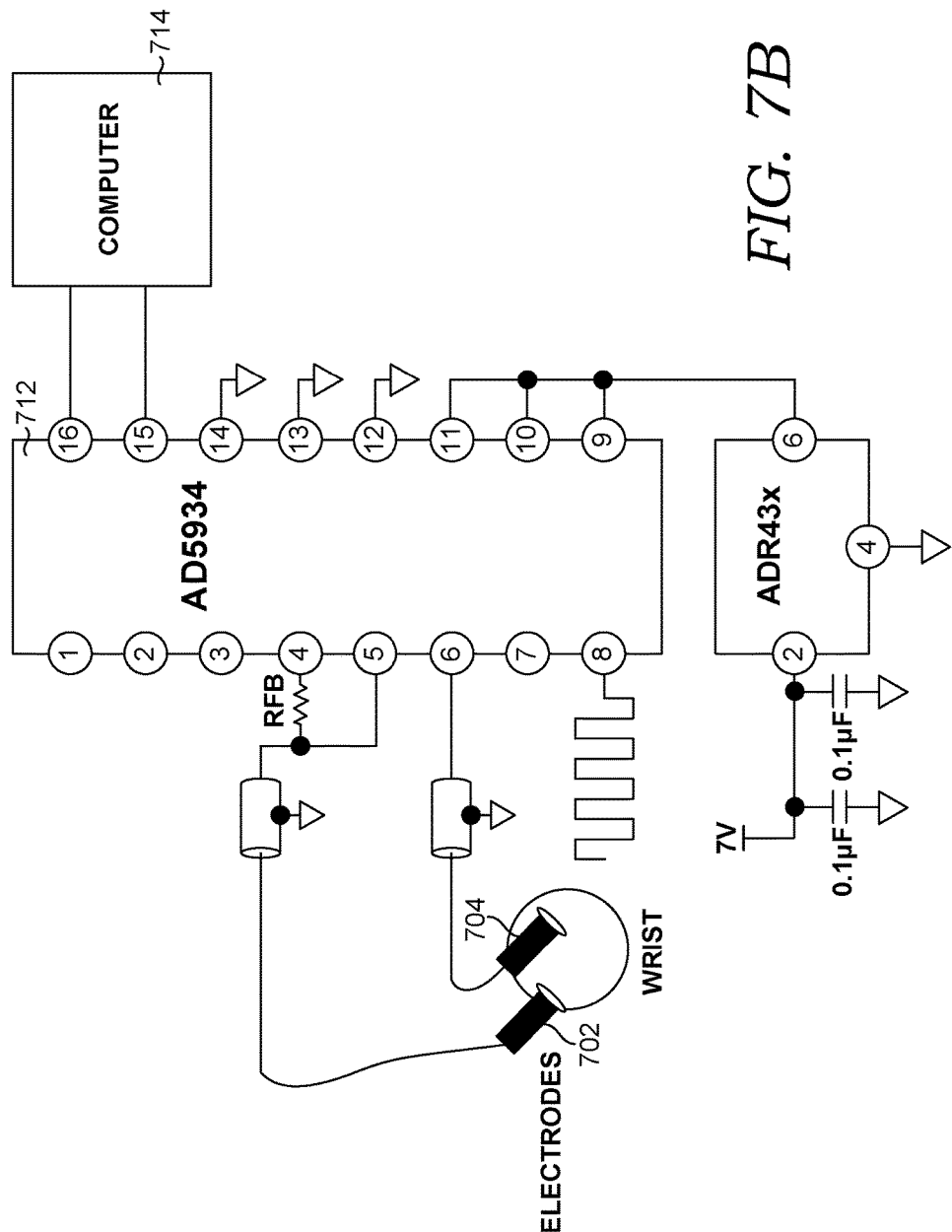

Turning briefly to FIGS. 7A and 7B, an example embodiment of monitor 141 is shown. In this embodiment, monitor 141 is worn on the subject's wrist and may be embodied as a smart watch or fitness tracker with the one or more sensors.

Returning to FIG. 1A, computer system 120 comprises one or more processors operable to receive instructions and process them accordingly. Computer system 120 may be embodied as a single computing device or multiple computing devices communicatively coupled to each other. In one embodiment, processing actions performed by computer system 120 are distributed among multiple locations such as one or more local clients and one or more remote servers and may be distributed across the other components of example operating environment 100. For example, a portion of computer system 120 may be embodied on monitor 141 or manager 140 for performing signal conditioning of the measured subject variables, such as bioimpedance. In one embodiment, computer system 120 comprises one or more computing devices, such as a server, desktop computer, laptop, or tablet, cloud-computing device or distributed computing architecture, a portable computing device such as a laptop, tablet, ultra-mobile P.C., or a mobile phone.

Embodiments of computer system 120 include computer software stack 125, which in some embodiments operates in the cloud, as a distributed system on a virtualization layer within computer system 120, and includes operating system 129. Operating system 129 may be implemented as a platform in the cloud and is capable of hosting a number of services such as 122, 124, 126, and 128. Some embodiments of operating system 129 comprise a distributed adaptive agent operating system. Embodiments of services 122, 124, 126, and 128 run as a local or distributed stack in the cloud, on one or more personal computers, or servers such as computer system 120, and/or a computing device running interfaces, such as interfaces 140 and 142. In some embodiments, interface 142 operates in conjunction with computer software stack 125.

In embodiments, model variables indexing service 122 provide services that facilitate retrieving frequent item sets, extracting database records, and cleaning the values of variables in records. For example, service 122 may perform functions for synonymic discovery, indexing or mapping variables in records, or mapping disparate medical systems' ontologies, such as determining that a particular medication frequency of a first record system is the same as a second record system. In some embodiments, these services may invoke computation services 126. Predictive models service 124, in general, is responsible for providing models for determining abnormal hydration status in subjects, such as described in connection to method 200 of FIG. 2A and method 250 of FIG. 2B. Predictive models service 124 may use one or more evolutionary algorithms, such as PSO and DE, to make abnormal hydration status predictions.

Computation services 126 perform statistical software operations and include statistical calculation packages such as, in one embodiment, the R system (the R-project for Statistical Computing, which supports R-packages or modules tailored for specific statistical operations and which is accessible through the Comprehensive R Archive Network (CRAN) at http://cran.r-project.org) or similar services. In an embodiment, computation services 126 include the services or routines, which may be embodied as one or more software agents or routines, such as the example embodiments of computer program routines illustratively provided in FIGS. 4A-4D. In some embodiments, computation services 126 use EMRs, lab information, or monitor 141 information (such as from a subject-worn sensor) provided by a stream processing service 128.

Some embodiments of computer software stack 125 may further use Apache Hadoop and Hbase framework (not shown) or similar frameworks operable for providing a distributed file system and facilitating access to cloud-based services such as those provided by Cerner Healthe Intent®. Additionally, some embodiments of computer software stack 125 may further comprise one or more services stream processing service(s) 128. For example, such stream processing service(s) may be embodied using IBM InfoSphere stream processing platform, Twitter Storm stream processing, Ptolemy or Kepler stream processing software, or similar complex event processing (CEP) platforms, frameworks, or services, which may include the user of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (also referred to as data store), which in some embodiments includes subject data for a candidate or target subject (or information for multiple subjects), including raw and processed subject data; variables associated with subject recommendations; recommendation knowledge base; recommendation rules; recommendations; recommendation update statistics; an operational data store, which stores events, frequent item sets (such as "X often happens with Y", for example), and item sets index information; association rule bases; agent libraries, solvers and solver libraries, and other similar information including data and computer-usable instructions; subject-derived data; and medical provider information, for example. It is contemplated that the term "data" includes any information that can be stored in a computer-storage device or system, such as user-derived data, computer-usable instructions, software applications, or other information. In some embodiments, storage 121 comprises the data store(s) associated with EMR system 160. Further, although depicted as a single storage data store, storage 121 may comprise one or more data stores, or may be in the cloud.

Figure 1B:
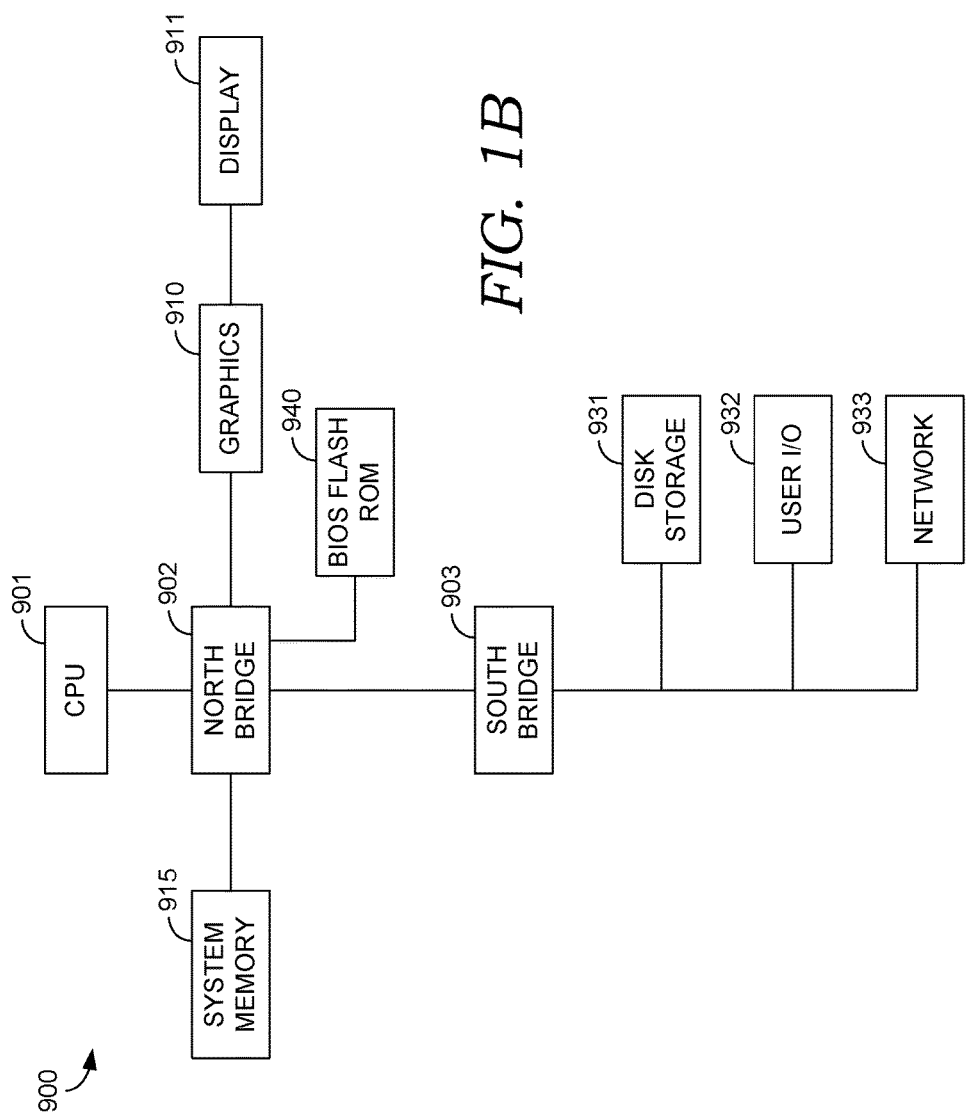

Turning briefly to FIG. 1B, there is shown one example embodiment of computing system 900 that has software instructions for storage of data and programs in computer-readable media. Computing system 900 is representative of a system architecture that is suitable for computer systems such as computer system 120. One or more CPUs, such as 901, have internal memory for storage and couple to the north bridge device 902, allowing CPU 901 to store instructions and data elements in system memory 915 or memory associated with graphics card 910, which is coupled to display 911. Bios flash ROM 940 couples to north bridge device 902. South bridge device 903 connects to north Bridge device 902, allowing CPU 901 to store instructions and data elements in disk storage 931, such as a fixed disk or USB disk, or to make use of network 933 for remote storage. User I/O device 932, such as a communication device, a mouse, a touch screen, a joystick, a touch stick, a trackball, or keyboard, also couples to CPU 901 through south bridge 903. The system architecture depicted in FIG. 1B is provided as one example of any number of suitable computer architectures, such as computing architectures that support local, distributed, or cloud-based software platforms and that are suitable for supporting computer system 120.

Returning to FIG. 1A, in some embodiments, computer system 120 is a system made up of one or more computing devices. In some embodiments, computer system 120 includes one or more software agents and, in an embodiment, includes an adaptive multi-agent operating system, but it will be appreciated that computer system 120 may also take the form of an adaptive single agent system or a non-agent system. Computer system 120 may be a distributed computing system, a data processing system, a centralized computing system, a single computer, such as a desktop or laptop computer or a networked computing system.

Figure 2A:
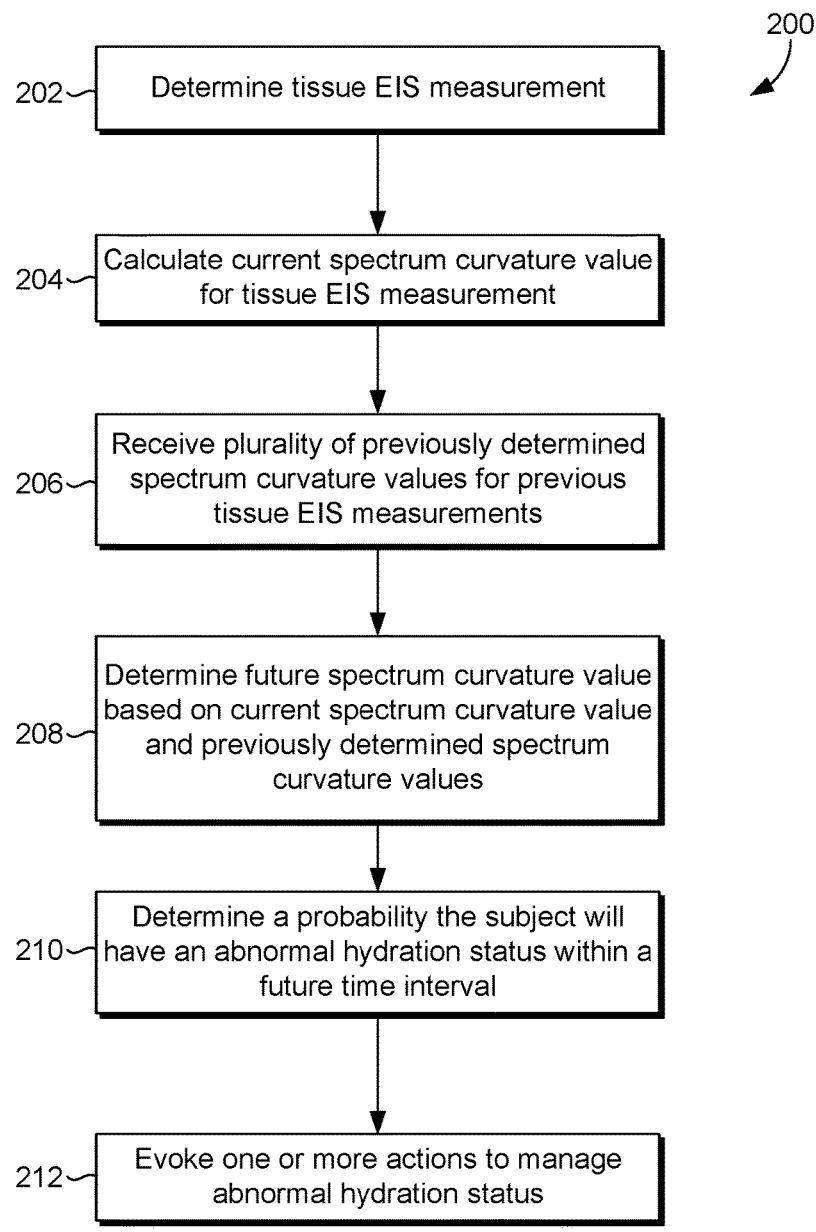
FIGS. 2A and 2B depict flow diagrams of methods for forecasting user hydration status, in accordance with an embodiment of the invention.
Figure 2B:
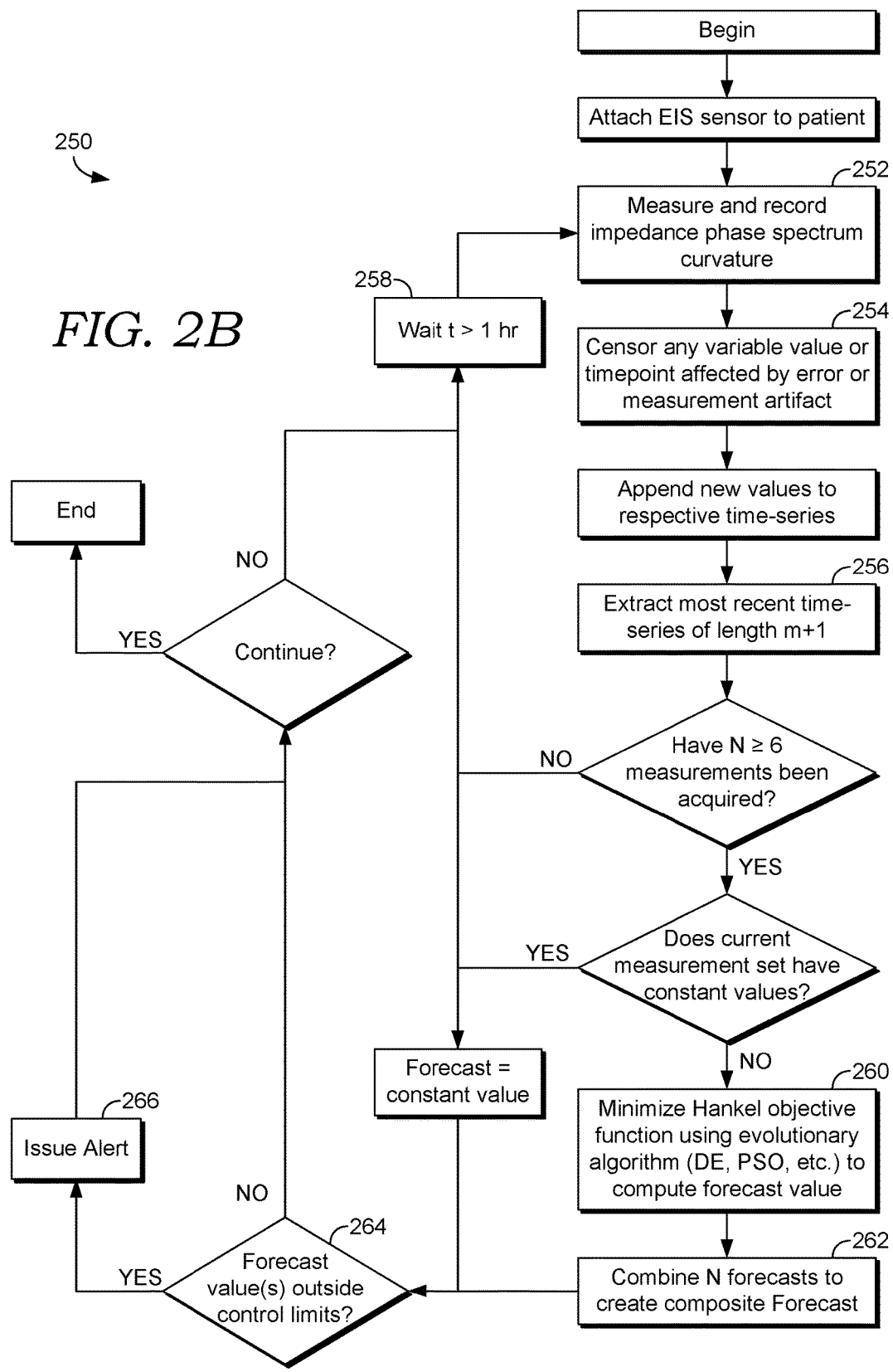

Turning now to FIGS. 2A-2B, flow diagrams illustrating example methods for forecasting a subject's hydration status are provided. For instance, FIG. 2A depicts method 200 for predicting an abnormal hydration status in a subject. An abnormal hydration status may include dehydration or overhydration. An abnormal hydration status may further be related to other medical conditions such as hypovolemia, progression of diabetes, congestive heart failure, infection or sepsis, an inflammatory response, renal disease, dialysis, psychiatric illness, stroke, dementia, exposure to chemical or biological agents, and administration of a systemically, regionally or locally applied pharmaceutical or other therapy. An abnormal hydration status may also be related to athletic exertion.

At step 202, a current tissue EIS measurement is determined from one or more received physiological levels of the subject. The physiological levels may be bioimpedance data acquired from a monitor, such as monitor 141 discussed with FIG. 1 and device 700 described below with respect to FIGS. 7A and 7B. A tissue impedance level may be received for a plurality of pre-determined frequencies to develop the EIS measurement. A current curvature value may be calculated for the current tissue EIS measurement at step 204. The curvature value may be determined from a phase spectrum, a magnitude spectrum, or a complex impedance spectrum representing both phase and magnitude. In some embodiments, it is desired to use impedance phase spectrum, which has been found to be particularly sensitive to changes, as discussed further below with respect to FIG. 3.

Method 200 also involves receiving a plurality of previously determined curvature values for previous tissue EISs for the subject, which is represented at step 206. The plurality of previously determined curvature values may correspond to a plurality of time-stamped data points. These data points may be for time intervals immediately preceding a time interval in which the data for the current tissue EIS measurement is acquired.

At step 208, a future curvature value for the subject at a future time interval is determined to forecast or predict an abnormal hydration status. With reference generally to method 200 of FIG. 2A and FIGS. 4A-4D, time series forecasting is a challenge in many fields of science and engineering. Many techniques exist for time series forecasting. In general, the object of these techniques is to build a model of the process and then use this model on the last values of the time series to extrapolate past behavior into future. Forecasting procedures include different techniques and models. Moving averages techniques, random walks and trend models, exponential smoothing, state space modeling, multivariate methods, vector autoregressive models, cointegrated and causal models, methods based on neural, fuzzy networks or data mining and rule-based techniques are typical methods used in time series forecasting.

Embodiments of the invention involves a new method for the identification of an optimal set of time lags based on non-uniform attractor embedding from the observed nonlinear time series is presented. In an embodiment, a simple, deterministic method for the determination of non-uniform time lags comprises the pre-processing stage of the time series forecasting algorithm.

A near-optimal set of time lags is determined by evolutionary algorithms, such as Particle Swarm Optimization (PSO) or Differential Evolution (DE). The solution fitness objective function may be constructed in such a way that it represents the spreading of the attractor in the delay coordinate space but does not contain any information on prediction error metrics. A weighted one-point crossover rule enables an effective identification of near-optimal sets of non-uniform time lags which are better than the globally optimal set of uniform time lags. Thus, the reconstructed information on the properties of the underlying dynamical system is directly elaborated in the prediction system and method.

In forecasting physiologic variables, the method discerns the "skeleton algebraic sequences" associated with short-term time series of the variables. The concept of the rank of the Hankel matrix is exploited to detect a base algebraic fragment of the time series. Particle swarm optimization and evolutionary algorithms are then used to remove the noise and discern the skeleton algebraic sequence that characterizes the time series and the underlying dynamical physiologic system that gives rise to the series.

The Hankel matrix H(m) is constructed from the elements of the time series sequence $x = \{x_0, x_1, x_2, \ldots, x_k\}$:

$$H^{(m)} = \begin{bmatrix} x_0 & x_1 & \ldots & x_{m-1} \\ x_1 & x_2 & \ldots & x_m \\ \vdots & & \ddots & \vdots \\ x_{m-1} & x_m & \ldots & x_{2m-2} \end{bmatrix} \quad \text{(Eq. 1)}$$

Determinants of Hankel matrices are denoted by det H(m). The rank of the sequence x is an integer m that satisfies the following conditions:

$$\det H^{(m+k)} = 0 \text{ and } \det H^{(m)} \neq 0, \text{ for all } k. \quad \text{(Eq. 2)}$$

If x is a completely chaotic, random sequence then $m = \infty$ (the sequence does not have a defined finite rank). However, if the sequence is not random and arises from an algebraic evolutionary process, then the following equality holds:

$$x_n = \Sigma_{k=1}^r \Sigma_{l=0}^{n_k-1} \mu_{kl}(l^n) \rho_k^{n-1},$$ (Eq. 3)

where the characteristic roots $\rho k$, $k=1, 2, \ldots, 4$ can be determined from the Hankel characteristic equation:

$$\det = \begin{bmatrix} x_0 & x_1 & \ldots & x_m \\ x_{m-1} & x_m & \ldots & x_{2m-1} \\ \vdots & & \ddots & \vdots \\ 1 & \rho & \ldots & \rho^m \end{bmatrix} = 0$$ (Eq. 4)

where the coefficients $\mu_{kl}$ can be determined from a system of linear algebraic equations (3) for different values of n.

Due to natural imprecision of measurement and various sources of noise in physiologic signals, the assumption that a sequence of such measurements is an algebraic evolution is, at best, an approximation. The forecasting of the next element $x_{2n}$ from (1) and (2) is not in general possible due to the inherent superimposed noise in real-world time series. Therefore, one embodiment proposes a set of adjustment or noise-compensating error terms $\varepsilon i$, such that the next (seventh) element to be forecast in a 6-element time series represented by a 4×4 Hankel matrix is:

$$x[4, 4] = ((ace - ad \wedge 2 + bcd - eb \wedge 2 + bcd - c \wedge 3) \wedge (-1) *$$ (Eq. 5)
$$(-d(bdf - be \wedge 2 + cde - fc \wedge 2 + cde - d \wedge 3) +$$
$$e(adf - ae \wedge 2 + ec \wedge 2 - bcf + bde - cd \wedge 2) -$$
$$f(acf - ade + bce - fb \wedge 2 + bd \wedge 2 - dc \wedge 2))$$

where
$$a = x[1, 1] + \varepsilon\_1$$
$$b = x[1, 2] + \varepsilon\_2$$
$$c = x[1, 3] + \varepsilon\_3$$
$$d = x[1, 4] + \varepsilon\_4$$
$$e = x[2, 4] + \varepsilon\_5$$
$$f = x[3, 4] + \varepsilon\_6$$

One embodiment sets forth an optimization fitness objective function to minimize, illustrated for the case of a sequence that is 6 elements in length:

$$F(x, \vec{e}) = \text{abs}\left[\det(x) * \left(\frac{1}{6} * \sum_1^6 \text{abs}(e_i) + \text{abs}(x[4, 4] - EWMA(x))\right)\right]^{-1}$$ (Eq. 6)

where EWMA is an exponentially-weighted moving average of the subset of the already-acquired elements in the sequence upon which the forecast is to be based.

Accordingly, the future curvature value may be determined from the current curvature value and the plurality of previously determined curvature values by using one or more evolutionary algorithms, such as PSO or DE. Specifically, an evolutionary algorithm may be used to minimize an objective function may be minimized or a determinant of a Hankel matrix representing the current curvature value and the plurality of previously determined curvature values. The employment of evolutionary algorithms for the identification of the closest (smallest F(x,e)) algebraic skeleton sequences enables the system and method to achieve relatively high-quality predictions with sequences as short as 4 to 8 elements in length. The method is free of any assumptions regarding any statistical or physiologic dynamical properties of the measurements but instead performs local individual identification of the skeleton algebraic progression for every time step.

Continuing with method 200, a probability the subject will have an abnormal hydration status within the future time interval may be determined based on the future curvature value and, in some embodiments, one or more predetermined threshold values, which is represented as step 210 in FIG. 2A. In some embodiments, the probability represents a risk of acute deterioration in hydration status with a future time interval. The predetermined threshold values may be represented as percentages of normal curvature values, which represented the curvature of an EIS spectrum for a normal state of hydration. In some embodiments, there is an upper threshold limit and a lower threshold limit, and an abnormal hydration status may be indicated when the future curvature value is outside those thresholds. The normal curvature values may be based on a population of people or may be specific to the subject. For instance, normal curvature values may be based on previous impedance data received from a monitor, such as monitor 141 in FIG. 1, associated with the subject. Additionally, the normal values may be received from the subject's EMR. Normalizing threshold values based on the specific subject increases the accuracy of the method.

At step 212, upon determining the probability that the subject will have an abnormal hydration status within the future time interval, one or more actions may be evoked to manage the abnormal hydration status. Such actions may include initiating a signal that causes an alert to be presented to the subject; initiating a signal that causes an alert to be presented to a medical professional associated with the subject; automatically increasing a rate of monitoring the subject, and automatically allocating one or more treatments to reduce risks associated with the abnormal hydration status. Another action may include providing one or more recommendations to the subject for managing the risk of abnormal hydration status. For instance, a recommendation to consume fluids may be given after a certain probability of dehydration is determined.

FIG. 2B provide another flow diagram illustrating a similar method 250 for predicting abnormal hydration status. In particular, the example method 250 comprises a process for acquiring the necessary data elements, the data flow for computing forecast values from these, and the logic and steps for combining successive forecasts into a composite to be communicated to appropriate medical professionals who are responsible for the care of the subject. As shown in FIG. 2B, at step 252, after a sensor capable of acquiring EIS data is attached to a subject, such as putting on a wearable bracelet having EIS sensors, an impedance phase spectrum curvature may be measured and recorded. In some embodiments, values or time points affected by error or measurement artifact may be censored, or detected and removed, at step 254 such that possible noise will impact the forecasting method. A new or current value for the EIS curvature may be appended to a time series comprising previously determined curvatures values. At step 256, the most recent time series may be extracted, and it is determined whether the length of the time series, as indicated by the number of measurements, is sufficient to accurately forecast future curvature values. In the embodiment illustrated in FIG. 2B, there must be at least 6 measurements, and if the time series comprises less than 6 measurements, the method includes waiting a period of time, such as an hour, to acquire new data, shown as step 258. In other embodiments, there must be at least 4 measurements. In this case, a future value may be predicted from the current curvature measurement and 3 previously determined curvature measurements.

If there are a sufficient number of measurements, the method continues on to forecasting future curvature values. If the curvature values in the time series are constant, then the forecasted curvature value is the constant value. However, if the measurements are not constant, at step 260, a forecast value is computed by minimizing Hankel objective function using evolutionary algorithms.

In some embodiments, at step 262, a plurality of forecasted or future curvature values is combined to create a composite forecast. The plurality of forecasted or future curvature values may be for successive future time intervals. Combining future curvature values may be done by calculating an arithmetic mean or a median of the values, an exponentially weighted moving average or other linear combination of the values, or a minimum or a maximum of the values. Combining the values may further include applying a digital filter to the values.

Next, in step 264, the future or forecast curvature values are compared to control limits, such as the predetermined thresholds previously discussed. The curvature values used may include the composite forecast and/or one or more of the future curvature values determined. If the forecast values are not outside the control limits, there is no indication of a probable abnormal hydration status, and the monitoring process may continue. If, however, the forecast values are outside the limits, an alert may be issued, shown as step 266. Upon issuing an alert or evoking another action, monitoring may continue as normal or the monitoring may be adjusted based on the abnormal hydration status. For instance, the frequency with which measurements are taken may be increased to more closely monitor any changes in the subject's hydration status.

Turning now to FIGS. 7A and 7B, one example device is provided in accordance with an embodiment of the invention reduced-to-practice. Device 700 may act as a monitor, such as monitor 141 discussed above with reference to FIG. 1A. The reduced-to practice embodiment of device 700 includes a two-electrode 702 and 704 sensor comprised of 1-cm square 11-ga 316 stainless steel electrode surfaces 706 and 708 having an unpolished mill finish, annealed and conforming to ASTM A240. Some embodiments utilize a separation of multiple centimeters distance between a plurality of at least two electrodes 702 and 704. In the case of the example embodiment reduction to practice, the electrodes 702 and 704 of device 700 were incorporated into a non-conductive elastomeric band 710 (also referred to as a bracelet) worn at the subject's wrist. The 1 cm square #316 brushed stainless steel electrode surfaces 706 and 708 were affixed to opposing aspects of the internal circumference of the band 710 in such a manner that one electrode 702 was centered on the volar/flexor side proximal to the flexor retinaculum and the other electrode 704 was centered directly opposite on the extensor side of the wrist. Accordingly, the corresponding 1 cm square #316 brushed stainless steel electrode surfaces 706 and 708 are positioned on opposing sides of the subject's wrist when the band 710 is being worn. In this configuration, the tissues between the electrodes 702 and 704 are a mixture comprised mainly of bone, bone marrow, ligaments, tendons, fat, other connective tissue, skin, and subcutaneous tissue. Relatively little muscle tissue or nerve tissue is enclosed in the space (except for the extensor pollicis brevis and extensor indicis proprius bellies), and relatively little blood or blood vessels are contained there. As such, the EIS obtained from this electrode configuration is dominated by the properties of deep tissues, not by "skin" impedance, which is mainly in superficial locations less than 1 mm deep.

The electrodes 702 and 704 were utilized in a "dry" condition (without electrode gel). The electrodes 702 and 704, in conjunction with their corresponding stainless steel electrode surfaces 706 and 708, were apposed to the skin under minimal compression with a silastic silicone rubber band 710 constructed with a cavity to enclose the circuit boards to which the stainless steel electrode surfaces 706 and 708 were affixed. An Analog Devices Inc. (One Technology Way, Norwood, Mass.) AD5934 chip 712 was used to provide sawtooth ramp coverage of excitation frequencies between 3 KHz and 300 KHz to elicit an EIS spectrogram at 9 frequencies. The chip 712 was also used for acquisition of tissue electrical impedance magnitude and phase at each frequency in the spectrogram signal. The chip 712 includes a 12-bit 250 Ksample/sec analog-to-digital converter (ADC) whose output was stored during each bout of measurement.

The digital impedance data were stored in flash memory on the PCB in proximity to the signal generator and impedance ADC chips and subsequently transferred to a general-purpose laptop computer 714 for processing. In the illustrative embodiment, impedance 50 ramp cycles acquired in each 60-sec measurement bout were averaged to produce an EIS having substantially reduced through-tissue impedance magnitude noise and phase noise compared to a single-ramp spectrum acquisition. The signal averaging also afforded a degree of robustness against impedance bias artifact arising from inadvertent subject limb motion during a measurement bout. Impedance magnitude and phase as a function of frequency were calculated by the AD5934 chip 712 via Fourier transform and AC phasor trigonometric relationships as are customary in the art. Telemetry of the acquired magnitude and phase data were performed via USB serial interface.

Figure 5B:
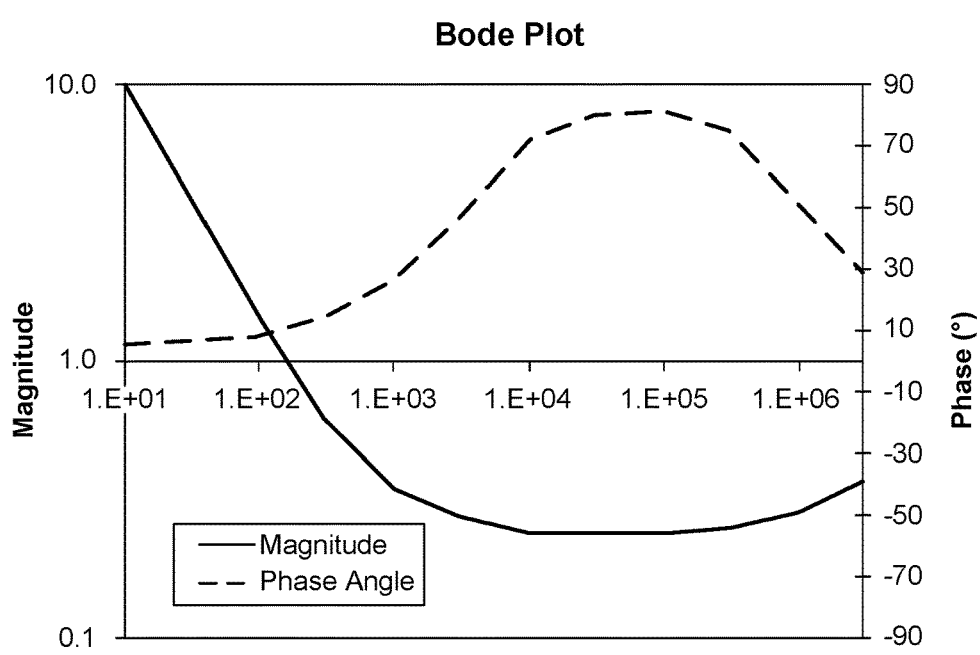

With reference again to FIGS. 2A-2B and continuing reference to FIGS. 1A-B, 4A-5B and 7A-7B an example embodiment of the invention was reduced-to-practice for testing and analysis using the device described in connection to FIGS. 7A and 7B. The example embodiment used a server cluster running the Linux operating system, the open-source statistical software package R, and the R module PSO. A set of de-identified, secondary-use-consented, EMR-derived, HIPAA-compliant vital signs measurements from 181 individuals whose care episodes had previously been completed and for whom the dehydration outcomes were already known was extracted from a commercially-available data warehouse (Cerner Health Facts®). EIS time-series were computed for each of the 181 subjects and next-value forecasts were generated using PSO. (FIG. 5B shown one example of an actual person's EIS phase spectrum curvature time series over the course of one day, where calculations are alternatively performed by the differential evolution (DE) or by particle swarm optimization (PSO) method.)

As expected, the electrical impedance spectrogram for the absolute magnitude of the impedance was quite sensitive to body temperature, to perspiration in the skin area where the sensor was applied, to duration of wearing the sensor, and to motion artifact. However, the curvature of the electrical impedance phase spectrum was comparatively insensitive to these factors and to motion artifact.

Curvature of the electrical impedance phase spectrum [on 'fairing' or 'fairness' of the curve] was determined by calculating the discrete sum of a second-order difference equation of at least 4 frequency points in the spectrum. It is known that the degree of curvature of a curve between two points $\omega_1$ and $\omega_2$ is well characterized by the integral of the second derivative of the curve.

$$\text{curvature} \approx \int_{\omega_1}^{\omega_2} \frac{d^2u}{du^2} d\omega \qquad (\text{Eq. 7})$$

Associated aspects of curvature determinations include the following properties:
 1. A curve is termed 'fair' if its curvature plot is continuous and consists of only a few monotone pieces.
 2. A frequency analysis of the radius of curvature plotted against arc length yields a measure of fairness; the lower the dominant frequency, the fairer the curve.
 3. A fair curve is one that has a minimum strain energy.
 4. A curve is termed 'fair' if it can be drawn with a small number of French curve segments.
 5. A curve's curvature plot must be almost piecewise linear, with only a small number of segments.
 6. The curve should be convexity preserving.
 7. A curve is termed 'fair' if its curvature plot (a) is continuous, (b) has the appropriate sign (if the convexity of the curve is prescribed), and (c) is approximated by a piecewise monotone function with as few monotone pieces as possible.
 8. Fairness is measured as the integral of the square of the second derivative of the curve; generally, the lower this integral is the fairer the curve.
 9. The gentleness or gradualness of development of curvature along a curve is a measure of curve fairness. The lower the local rate of change of fairness, the fairer the curve.
 10. A curve is fair if its curvature plot consists of relatively few monotone pieces.
 11. Fairness measures depend only on the geometric invariants of the curve and are independent of the curve's parametrization. A fair curve should minimize either the variation of the radius of curvature or the variation of curvature.
 12. A curve is called fair if three conditions are satisfied: (1) the curve is G2; (2) there are no unwanted inflection points on the curve; (3) the curvature varies in an even, slowly-changing manner. Expanding on (3): (i) the number of extreme points of the curvature should be small; (ii) the curvature between any two adjacent extreme points should vary almost linearly.
 13. A curve is called fair if its logarithmic curvature graph has an almost constant gradient.

From the example embodiment of the invention reduced to practice, it was found that, in states of abnormal hydration, the curvature of the phase spectrum departs significantly from the range of phase spectrum curvature values associated with the normal, healthy state.

Figure 3:
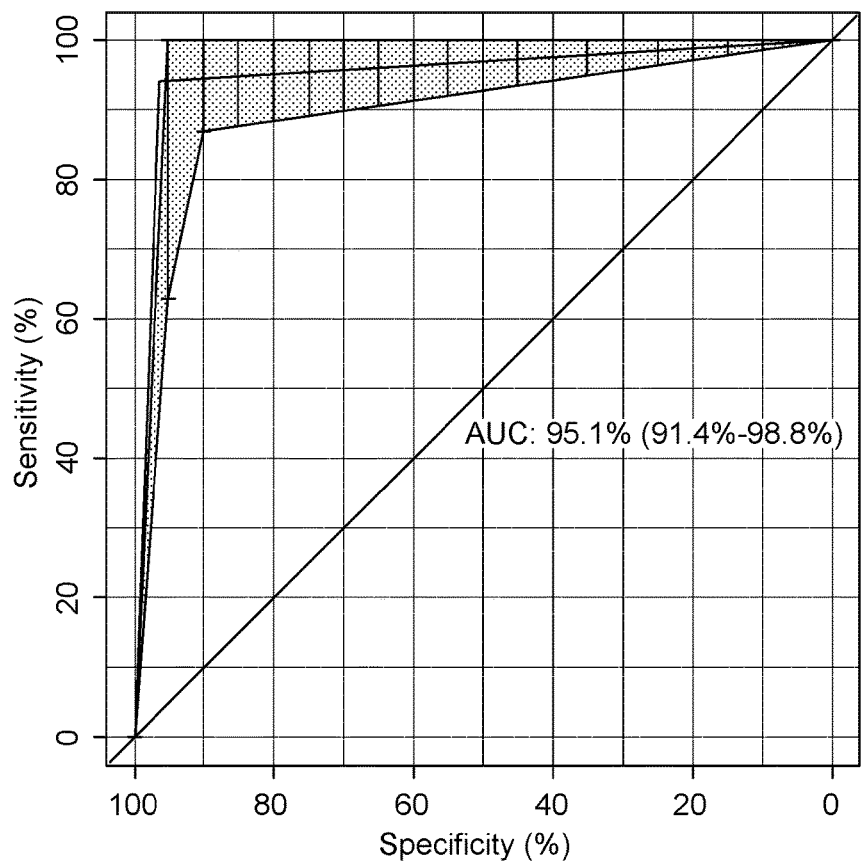
FIG. 3 depicts a Receiver Operating Characteristic (ROC) curve representing the accuracy of the forecasting system and method, in accordance with an embodiment of the invention.

For PSO-forecast electrical impedance phase spectrum curvature values denoting dehydration or, alternatively, overrhydration, the statistical sensitivity, specificity, and ROC area-under the curve (AUC) were computed (see FIG. 3).

In the data acquired during the reduction-to-practice study, the Mean Absolute Percentage Error (MAPE):

$$MAPE = \frac{100}{N} \sum_{1}^{N} |x_i - \hat{x}_i| \qquad (\text{Eq. 8})$$

for time series of length 6 was in the range 13% to 26% for the EIS phase spectrum curvature time series to which the invention has been applied. As such, the forecast is sufficiently accurate to serve as an effective advisory aid to physicians wishing to ascertain the approximate risk that the subject will deteriorate (e.g., dehydration >5% of total body water) within a time frame comparable to the frequency with which the successive EIS measurements are being acquired. Conversely, the forecasts appear also to be sufficiently accurate to serve as an indication that therapeutic maneuvers that have already been undertaken have been effective or adequate (no dehydration event) for the recovery of the subject.

With further reference to FIG. 3, a receiver operating characteristic (ROC) curve of the forecasting system and method set forth in an embodiment of the invention, as applied to the computation of forecasts for hydration status. As is known to those practiced in the art, the area under the ROC curve is a standard means of quantitatively assessing a classifier model's discrimination, the degree to which the model is able to accurately categorize cases into one or the other of two classes or categories—in this instance, dehydration vs. euhydration. The table provided below provides the statistical properties of the prognostic system and method in the population of subjects in whom an embodiment of the invention was reduced to practice and validated.

| Item | Value |
| --- | --- |
| Sensitivity | 94% |
| Specificity | 96% |
| Event Prevalence | 28% |
| Positive Predictive Value (PPV) | 90% |
| Negative Predictive Value (NPV) | 98% |
| False Positive Rate | 9.6% |
| False Negative Rate | 2.3% |

Embodiment 1

One or more computer-readable media having computer-readable instructions embodied thereon that, when executed, facilitate a method for predicting an abnormal hydration status in a subject, the method comprising: determining a tissue electrical impedance spectroscopic (EIS) measurement from one or more received physiological levels of a subject; calculating a current spectrum curvature value based on the tissue EIS measurement; receiving a plurality of previously determined spectrum curvature values determined from previous tissue EIS measurements for the subject, the plurality of previously determined spectrum curvature values corresponding to a plurality of time-stamped data points; inferring a future spectrum curvature value for the subject at a future time interval by minimizing an objective function using one or more evolutionary algorithms based on the current curvature value and the plurality of previously determined spectrum curvature values; based on the inferred future spectrum curvature value and one or more predetermined threshold values, determining a probability that the subject will have an abnormal hydration status within the future time interval; and upon determining the probability that the subject will have an abnormal hydration status within the future time interval, evoking one or more actions to manage the abnormal hydration status.

Embodiment 2

The computer-readable media of claim 1, wherein the one or more actions comprises at least one of: initiating a signal that causes an alert to be presented to the subject; initiating a signal that causes an alert to be presented to a medical professional associated with the subject; automatically increasing a rate of monitoring the subject, and automatically allocating one or more treatments to reduce risks associated with the abnormal hydration status.

Embodiment 3

The computer-readable media of claim 1 or 2, wherein the plurality of time-stamped data points comprises at least three time-stamped data points.

Embodiment 4

The computer-readable media of any of claims 1-3, wherein the one or more evolutionary algorithms comprise at least one of particular swarm optimization and differential evolution.

Embodiment 5

The computer-readable media of any of claims 1-4, wherein the one or more predetermined thresholds are calculated as a percentage of a normal spectrum curvature value for the subject, the normal spectrum curvature value representing a normal hydration status.

Embodiment 6

The computer-readable media of any of claims claim 1-5, wherein the normal spectrum curvature value is based on the plurality of previously determined spectrum curvature values.

Embodiment 7

The computer-readable media of any of claims 1-6, wherein the normal spectrum curvature value is received from an electronic medical record (EMR) computer system, and wherein the one or more physiological levels comprise tissue electrical impedance levels measured at a plurality of frequencies.

Embodiment 8

The computer-readable media any of claims 1-7, wherein the one or more predetermined thresholds comprise an upper threshold and a lower threshold.

Embodiment 9

The computer-readable media of any of claims 1-8, wherein the tissue EIS measurement comprises a phase spectrum, and wherein the current curvature value for the tissue EIS measurement comprises a phase spectrum curve.

Embodiment 10

The computer-readable media of any of claims 1-9, wherein determining a probability the subject will have an abnormal hydration status with the future time interval is further based on a combined future spectrum curvature value calculated by combining the future spectrum curvature value and a plurality of additional future spectrum curvature values.

Embodiment 11

The computer-readable media of claim 10, wherein combining the future curvature value and the plurality of additional future spectrum curvature values comprise calculating one of the following: an arithmetic mean or a median of the values; an exponentially weighted moving average or other linear combination of the values; and a minimum or a maximum of the values.

Embodiment 12

A system for predicting an abnormal hydration status in a subject, the system comprising: one or more processors; one or more sensors configured to receive one or more physiological levels of a subject for determining tissue electrical impedance spectra of the subject; and computer-storage memory having computer-executable instructions stored thereon that, when executed by the one or more processors, implement a method comprising: determining a tissue electrical impedance spectroscopic (EIS) measurement of the subject; calculating a current spectrum curvature value for the tissue EIS measurement; receiving a plurality of previously determined spectrum curvature values for previous tissue EIS measurements for the subject, the plurality of previously determined spectrum curvature values corresponding to a plurality of time-stamped data points; determining a future spectrum curvature value for the subject at a future time interval by minimizing an objective function using one or more evolutionary algorithms based on the current spectrum curvature value and the plurality of previously determined spectrum curvature values; based on the future spectrum curvature value and one or more predetermined threshold values, determining a probability the subject will have an abnormal hydration status within the future time interval; and upon determining the probability that the subject will have an abnormal hydration status within the future time interval, evoking one or more actions to manage the abnormal hydration status.

Embodiment 13

The system of claim 12, wherein an abnormal hydration status is related to one or more of dehydration, overhydration, hypovolemia, progression of diabetes, congestive heart failure, infection or sepsis, an inflammatory response, renal disease, dialysis, psychiatric illness, stroke, dementia, exposure to chemical or biological agents, and administration of a systemically, regionally or locally applied pharmaceutical or other therapy.

Embodiment 14

The system of claim 12 or 13, wherein the one or more actions comprise at least one of: initiating a signal that causes an alert to be presented to the subject; initiating a signal that causes an alert to be presented to a medical professional associated with the subject; automatically increasing a rate of monitoring the subject, and automati-

Embodiment 15

The system of any of claims 12-14, wherein the one or more physiological levels comprise tissue electrical impedance levels measured at a plurality of frequencies.

Embodiment 16

The system of any of claims 12-15, wherein the one or more evolutionary algorithms comprise at least one of particular swarm optimization and differential evolution.

Embodiment 17

The system of any of claims 12-16, wherein minimizing the objective function comprises minimizing a determinant of a Hankel matrix representing the current spectrum curvature value and the plurality of previously determined spectrum curvature values.

Embodiment 18

A device for monitoring a subject for an abnormal hydration status, the device comprising: a processor; one or more sensors associated with the subject and configured to provide sensor data including at least physiological data for the subject; computer-storage memory having computer-executable instructions stored thereon that, when executed by the processor, implement a method comprising: determining a tissue EIS measurement of the subject; calculating a current spectrum curvature value based on the tissue EIS measurement; receiving a plurality of previously determined spectrum curvature values determined from previous tissue EIS measurements for the subject, the plurality of previously determined spectrum curvature values corresponding to a plurality of time-stamped data points; determining a future spectrum curvature value for the subject at a future time interval by minimizing an objective function using one or more evolutionary algorithms based on the current spectrum curvature value and the plurality of previously determined spectrum curvature values; based on the future spectrum curvature value and one or more predetermined threshold values, determining a probability the subject will have an abnormal hydration status within the future time interval; and upon determining the probability that the subject will have an abnormal hydration status within the future time interval, evoking one or more actions to manage the abnormal hydration status.

Embodiment 19

The device of claim 18, wherein the device further comprises a band wearable around the subject's wrist and wherein the one or more sensors comprise two electrode surfaces on the band and positioned on opposing sides of the subject's wrist.

Embodiment 20

The device of claim 18 or 19 further comprising a user interface to display information relating to the abnormal hydration status.

From the foregoing, it will be seen that the technology described in this disclosure is well adapted to attain all the ends and objects hereinabove set forth together with other advantages which are obvious and which are inherent to the structure. It will be understood that certain features and sub-combinations are of utility and may be employed without reference to other features and sub-combinations. This is contemplated by and is within the scope of the claims. Since many possible aspects of the technology are possible without departing from the scope thereof, it is to be understood that all matter herein set forth or shown herein and in the accompanying drawings is to be interpreted as illustrative and non-limiting.

What is claimed is:

1. A system for predicting an abnormal hydration status in a human subject, the system comprising:
   one or more processors;
   one or more sensors configured to receive one or more physiological levels of a subject for determining tissue electrical impedance spectra of the subject; and
   computer-storage memory having computer-executable instructions stored thereon that, when executed by the one or more processors, implement a method comprising:
   determining a tissue electrical impedance spectroscopic (EIS) measurement of the subject;
   calculating a value quantifying current spectrum curvature shape for the tissue EIS measurement;
   receiving a plurality of previously determined values quantifying spectrum curvature shape for previous tissue EIS measurements for the subject, the plurality of previously determined values quantifying spectrum curvature shape corresponding to a plurality of time-stamped data points;
   determining a future value quantifying spectrum curvature shape for the subject at a future time interval by minimizing an objective function using one or more evolutionary algorithms based on the value quantifying current spectrum curvature shape and the plurality of previously determined values quantifying spectrum curvature shape;
   based on the future value quantifying spectrum curvature shape and one or more predetermined threshold values, determining a probability the subject will have an abnormal hydration status within the future time interval; and
   upon determining the probability that the subject will have an abnormal hydration status within the future time interval, evoking one or more actions to manage the abnormal hydration status.

2. The system of claim 1, wherein an abnormal hydration status is related to one or more of dehydration, overhydration, hypovolemia, progression of diabetes, congestive heart failure, infection or sepsis, an inflammatory response, renal disease, dialysis, psychiatric illness, stroke, dementia, exposure to chemical or biological agents, and administration of a systemically, regionally or locally applied pharmaceutical or other therapy.

3. The system of claim 1, wherein the one or more actions comprise at least one of:
   initiating a signal that causes an alert to be presented to the subject;
   initiating a signal that causes an alert to be presented to a medical professional associated with the subject;
   automatically increasing a rate of monitoring the subject; and
   automatically allocating one or more treatments to reduce risks associated with the abnormal hydration status.

4. The system of claim 1, wherein the one or more physiological levels comprise tissue electrical impedance levels measured at a plurality of frequencies.

5. The system of claim 1, wherein the one or more evolutionary algorithms comprises at least one of particular swarm optimization and differential evolution.

6. The system of claim 1, wherein minimizing the objective function comprises minimizing a determinant of a Hankel matrix representing the current curvature value and the plurality of previously determined spectrum curvature values.

7. The system of claim 1, wherein the one or more processors, the one or more sensors, and the computer storage memory reside on a wearable device.

8. One or more computer-readable media having computer-readable
instructions embodied thereon that, when executed by a processor, facilitate a method for predicting an abnormal hydration status,
the method comprising:
determining, via a sensor, a tissue electrical impedance spectroscopic (EIS) measurement of a subject;
calculating a value quantifying current spectrum curvature shape for the tissue EIS measurement;
receiving a plurality of previously determined values quantifying spectrum
curvature shape for previous tissue EIS measurements for the subject, the plurality of previously determined values quantifying spectrum curvature shape corresponding to a plurality of time-stamped data points;
determining a future value quantifying spectrum curvature shape for the subject at a future time interval by minimizing an objective function using one or more evolutionary algorithms based on the value quantifying current spectrum curvature shape and the plurality of previously determined values quantifying spectrum curvature shape;
based on the future value quantifying spectrum curvature shape and one or more predetermined threshold values, determining a probability the subject will have an abnormal hydration status within the future time interval; and
upon determining the probability that the subject will have the abnormal
hydration status within the future time interval, evoking one or more actions to manage the abnormal hydration status.

9. The computer-readable media of claim 8, wherein the abnormal hydration status is related to one or more of dehydration, overhydration, hypovolemia, progression of diabetes, congestive heart failure, infection or sepsis, an inflammatory response, renal disease, dialysis, psychiatric illness, stroke, dementia, exposure to chemical or biological agents, or administration of a systemically, regionally or locally applied pharmaceutical or other therapy.

10. The computer-readable media of claim 8, wherein the one or more actions comprise at least one of:
initiating a signal that causes an alert to be presented to the subject;
initiating a signal that causes the alert to be presented to a medical professional associated with the subject;
automatically increasing a rate of monitoring the subject; or
automatically allocating one or more treatments to reduce risks associated with the abnormal hydration status.

11. The computer-readable media of claim 8, wherein the one or more evolutionary algorithms comprises at least one of particular swarm optimization or differential evolution.

12. The computer-readable media of claim 8, wherein minimizing the
objective function comprises minimizing a determinant of a Hankel matrix representing the current curvature value and the plurality of previously determined spectrum curvature values.

13. The computer-readable media of claim 8, wherein the one or more physiological levels comprise tissue electrical impedance levels measured at a plurality of frequencies.

14. The computer-readable media of claim 8, wherein the processor and the sensor reside on a wearable device.

15. A method for predicting an abnormal hydration status in a subject, the method comprising: determining, via one or more sensors, a tissue electrical impedance spectroscopic (EIS) measurement of the subject;
calculating, via one or more processors, a value quantifying current spectrum curvature shape for the tissue EIS measurement;
receiving a plurality of previously determined values quantifying spectrum curvature shape for previous tissue EIS measurements for the subject, the plurality of previously determined values quantifying spectrum curvature shape corresponding to a plurality of time-stamped data points;
determining a future value quantifying spectrum curvature shape for the subject at a future time interval by minimizing an objective function using one or more evolutionary algorithms based on the value quantifying current spectrum curvature shape and the plurality of previously determined values quantifying spectrum curvature shape;
based on the future value quantifying spectrum curvature shape and one or more predetermined threshold values, determining a probability the subject will have an abnormal hydration status within the future time interval; and upon determining the probability that the subject will have the abnormal hydration status within the future time interval, evoking one or more actions to manage the abnormal hydration status.

16. The method of claim 15, wherein the abnormal hydration status is related to one or more of dehydration, overhydration, hypovolemia, progression of diabetes, congestive heart failure, infection or sepsis, an inflammatory response, renal disease, dialysis, psychiatric illness, stroke, dementia, exposure to chemical or biological agents, or administration of a systemically, regionally or locally applied pharmaceutical or other therapy.

17. The method of claim 15, wherein the one or more actions comprise at least one of:
initiating a signal that causes an alert to be presented to the subject;
initiating a signal that causes the alert to be presented to a medical professional associated with the subject;
automatically increasing a rate of monitoring the subject; or automatically allocating one or more treatments to reduce risks associated with the abnormal hydration status.

18. The method of claim 15, wherein the one or more evolutionary algorithms comprises at least one of particular swarm optimization or differential evolution.

19. The method of claim 15, wherein minimizing the objective function comprises minimizing a determinant of a Hankel matrix representing the current curvature value and the plurality of previously determined spectrum curvature values.

20. The method of claim 15, wherein the one or more physiological levels comprise tissue electrical impedance levels measured ata plurality of frequencies.

21. The method of claim 15, wherein the one or more processors and the one or more sensors reside on a wearable device.

22. The method of claim 15, wherein the one or more physiological levels comprise tissue electrical impedance levels measured at a plurality of frequencies.

\* \* \* \* \*

UNITED STATES PATENT AND TRADEMARK OFFICE
CERTIFICATE OF CORRECTION

PATENT NO. : 10,405,810 B1
APPLICATION NO. : 15/162219
DATED : September 10, 2019
INVENTOR(S) : Douglas S. McNair Page 1 of 1

It is certified that error appears in the above-identified patent and that said Letters Patent is hereby corrected as shown below:

In the Specification

Column 17, Line 10: Please remove "det =" and replace with --det--.

In the Claims

Column 29, Line 6: Please remove "ata" and replace with --at a--.

Signed and Sealed this
Twenty-sixth Day of November, 2019

Andrei Iancu
*Director of the United States Patent and Trademark Office*